(12) United States Patent
Rearick et al.

(10) Patent No.: US 9,150,917 B2
(45) Date of Patent: Oct. 6, 2015

(54) METHODS, COMPOSITIONS AND SYSTEMS FOR SAMPLE DEPOSITION

(71) Applicant: LIFE TECHNOLOGIES CORPORATION, Carlsbad, CA (US)

(72) Inventors: Todd Rearick, Cheshire, CT (US); Jessica Lynn Reed, Newark, CA (US); Jason Gioia, Belmont, CA (US); Devin Dressman, Swampscott, MA (US); Nicholas Hapshe, Salem, MA (US); Brian Reed, Guilford, CT (US); John Andrew Sheridan, Marblehead, MA (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 14/057,450

(22) Filed: Oct. 18, 2013

(65) Prior Publication Data

US 2014/0100122 A1 Apr. 10, 2014

Related U.S. Application Data

(63) Continuation of application No. PCT/US2012/034358, filed on Apr. 20, 2012.

(60) Provisional application No. 61/477,358, filed on Apr. 20, 2011, provisional application No. 61/546,013, filed on Oct. 11, 2011, provisional application No. 61/585,019, filed on Jan. 10, 2012.

(51) Int. Cl.
| | |
|---|---|
| *C12Q 1/68* | (2006.01) |
| *B01L 3/00* | (2006.01) |
| *G01N 33/50* | (2006.01) |
| *G01N 33/543* | (2006.01) |

(52) U.S. Cl.
CPC ............ *C12Q 1/6874* (2013.01); *B01L 3/5085* (2013.01); *C12Q 1/6837* (2013.01); *G01N 33/50* (2013.01); *G01N 33/543* (2013.01); *B01L 2200/0642* (2013.01); *B01L 2200/0668* (2013.01); *B01L 2300/0819* (2013.01); *B01L 2300/0893* (2013.01)

(58) Field of Classification Search
None
See application file for complete search history.

(56) References Cited

U.S. PATENT DOCUMENTS

| | | | |
|---|---|---|---|
| 5,733,572 A * | 3/1998 | Unger et al. | 424/450 |
| 6,156,501 A | 12/2000 | McGall et al. | |
| 6,238,862 B1 | 5/2001 | McGall et al. | |
| 6,306,643 B1 | 10/2001 | Gentalen et al. | |
| 6,309,823 B1 | 10/2001 | Cronin et al. | |
| 6,429,027 B1 | 8/2002 | Chee et al. | |
| 6,544,732 B1 | 4/2003 | Chee et al. | |
| 6,576,425 B2 | 6/2003 | McGall et al. | |
| 6,620,584 B1 | 9/2003 | Chee et al. | |
| 6,705,754 B2 | 3/2004 | Winkler et al. | |
| 6,852,490 B2 | 2/2005 | Gentalen et al. | |
| 6,858,394 B1 | 2/2005 | Chee et al. | |
| 6,890,741 B2 | 5/2005 | Fan et al. | |
| 6,942,968 B1 | 9/2005 | Dickinson et al. | |
| 6,998,274 B2 | 2/2006 | Chee et al. | |
| 7,033,754 B2 | 4/2006 | Chee et al. | |
| 7,060,431 B2 | 6/2006 | Chee et al. | |
| 7,060,443 B2 | 6/2006 | McGall et al. | |
| 7,115,364 B1 | 10/2006 | Chee et al. | |
| 7,226,734 B2 | 6/2007 | Chee et al. | |
| 7,455,971 B2 | 11/2008 | Chee et al. | |
| 7,510,841 B2 | 3/2009 | Stuelpnagel et al. | |
| 7,563,576 B2 | 7/2009 | Chee et al. | |
| 7,582,420 B2 | 9/2009 | Oliphant et al. | |
| 7,612,020 B2 | 11/2009 | Stuelpnagel et al. | |
| 7,781,226 B2 | 8/2010 | McDevitt et al. | |
| 7,794,943 B2 | 9/2010 | McGall et al. | |
| 7,846,659 B2 | 12/2010 | Cronin et al. | |
| 7,901,897 B2 | 3/2011 | Stuelpnagel et al. | |
| 7,955,794 B2 | 6/2011 | Shen et al. | |
| 7,960,119 B2 | 6/2011 | Chee et al. | |
| 8,003,354 B2 | 8/2011 | Shen et al. | |
| 8,206,917 B2 | 6/2012 | Chee et al. | |
| 8,460,865 B2 | 6/2013 | Chee et al. | |
| 8,481,268 B2 | 7/2013 | Chee et al. | |
| 8,486,625 B2 | 7/2013 | Gunderson et al. | |
| 8,563,246 B2 | 10/2013 | Chee et al. | |
| 8,574,835 B2 | 11/2013 | Hinz et al. | |
| 8,586,312 B2 | 11/2013 | Gentalen et al. | |
| 8,628,952 B2 | 1/2014 | Stuelpnagel et al. | |
| 8,669,053 B2 | 3/2014 | Stuelpnagel et al. | |
| 8,795,967 B2 | 8/2014 | Chee et al. | |
| 2002/0001803 A1 | 1/2002 | Smith et al. | |

(Continued)

FOREIGN PATENT DOCUMENTS

| | | |
|---|---|---|
| WO | 2005012549 | 2/2005 |
| WO | 2005085855 | 9/2005 |

OTHER PUBLICATIONS

Invitation to Pay Additional Fees—Partial Search Report for Application No. PCT/US2012/034358, mailed Aug. 23, 2012, 6 pages.

Birren, et al., "Genome Analysis Laboratory Manual Series", B. Birren, ed., *Cold Spring Harbor Laboratory Press*, vols. 1-4, 1997-1999, 4 pages.

Diffenbach, et al., "PCR Primer, A Laboratory Manual", *Cold Spring Harbor Press*, 1995, 1995.

(Continued)

*Primary Examiner* — Juliet Switzer
*Assistant Examiner* — Sahana Kaup

(57) ABSTRACT

Methods, compositions, systems, apparatus, and kits are provided for depositing samples onto surfaces. The samples can include one or more particles, and the surface can include one or more reaction chambers. In some embodiments, the depositing can include the use of companion particles in combination with sample particles.

8 Claims, 7 Drawing Sheets

(56) References Cited

U.S. PATENT DOCUMENTS

| | | |
|---|---|---|
| 2004/0141880 A1 | 7/2004 | Handler et al. |
| 2005/0191620 A1* | 9/2005 | McDevitt et al. .......... 435/5 |
| 2006/0234267 A1 | 10/2006 | Besemer et al. |
| 2006/0257941 A1 | 11/2006 | McDevitt et al. |
| 2009/0026082 A1 | 1/2009 | Rothberg et al. |
| 2009/0127589 A1 | 5/2009 | Rothberg et al. |
| 2010/0137143 A1 | 6/2010 | Rothberg et al. |
| 2010/0197507 A1 | 8/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |

OTHER PUBLICATIONS

Hermanson, Greg T., "Bioconjugate Techniques", *Second Edition, Academic Press*, 2008, 1202 pages (will be uploaded in 12 parts due to size).

Merkus, Henk, "Particle Size Measurements", *Springer*, ISBN 978-1-4020-9015-8, 2009.

Rubinstein, M. et al., "Polymer Physics", *Oxford University Press*, ISBN-13: 978-0198520597, 2003.

Sambrook, et al., "Molecular Cloning: A Laboratory Manual", 3rd Ed., Ch. 8 *Cold Spring Harbor Laboratory Press, N.Y.*, 2001, 126 pages (will be uploaded in 5 parts due to size).

* cited by examiner

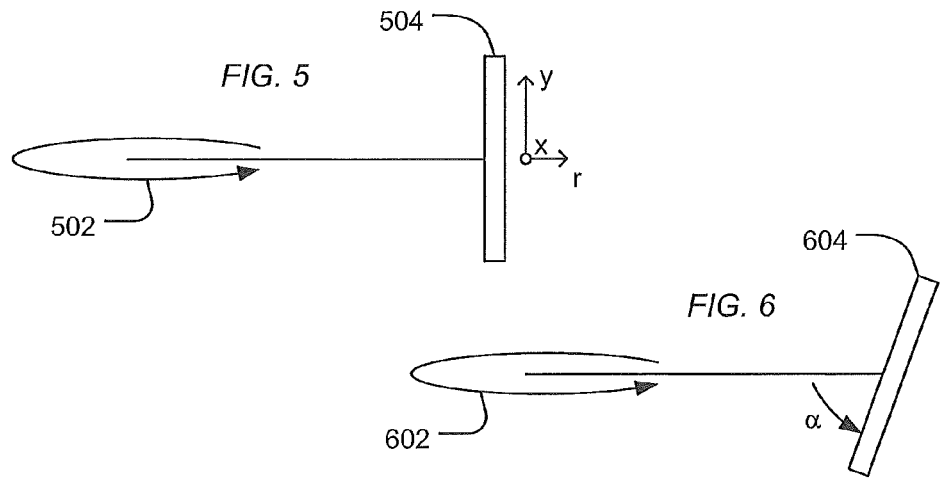
FIG. 5
FIG. 6
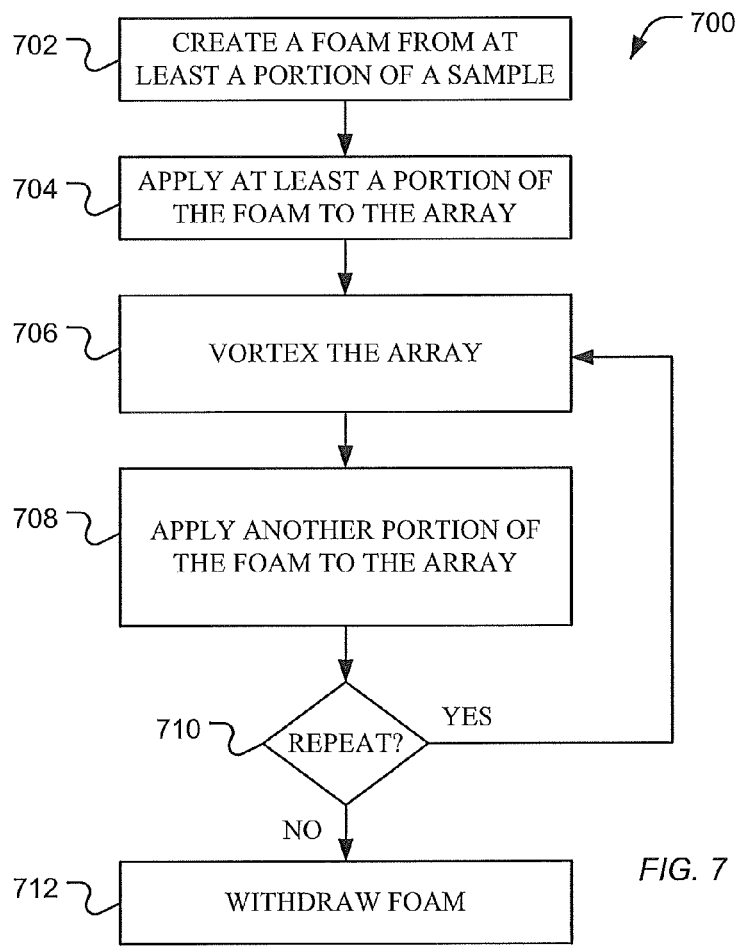
FIG. 7

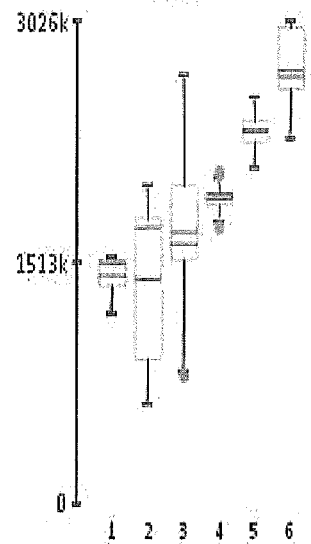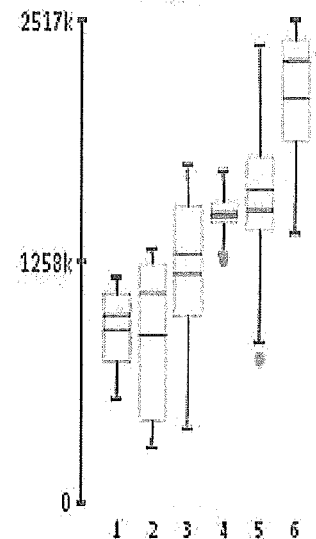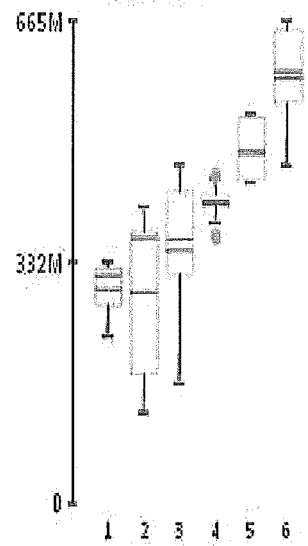

FIG. 8A — 100q17
FIG. 8B — 200q17
FIG. 8C — aq17bases

Tiger control 316 int 19 v VSV control 316 int 19 p-values: MWU [T-Test]
Tiger control 316 int 19 v TOBB 316 int 19 p-values: MWU [T-Test]
Tiger control 316 int 19 v PTOBB 316 int 19 p-values: MWU [T-Test]
Tiger control 316 int 19 v Short Chimera 316 int 19 p-values: MWU [T-Test]
Tiger control 316 int 19 v Chimera 316 int 19 p-values: MWU [T-Test]
[1] Tiger control 316 int 19 (N=5) mean (CV)
[2] VSV control 316 int 19 (N=5) mean (CV)
[3] TOBB 316 int 19 (N=5) mean (CV)
[4] PTOBB 316 int 19 (N=5) mean (CV)
[5] Short Chimera 316 int 19 (N=5) mean (CV)
[6] Chimera 316 int 19 (N=5) mean (CV)

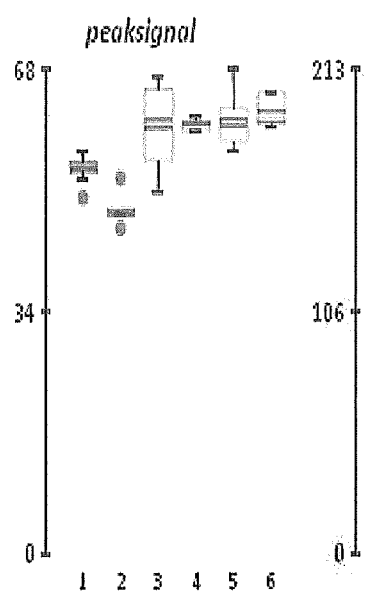

FIG. 9A
*peaksignal*

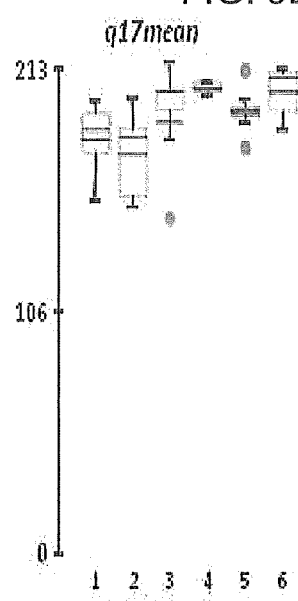

FIG. 9B
*q17mean*

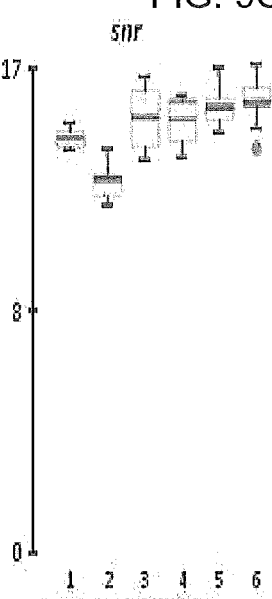

FIG. 9C
*snr*

Tiger control 316 int 19 v VSV control 316 int 19 p-values: MWU [T-Test]
Tiger control 316 int 19 v TOBB 316 int 19 p-values: MWU [T-Test]
Tiger control 316 int 19 v PTOBB 316 int 19 p-values: MWU [T-Test]
Tiger control 316 int 19 v Short Chimera 316 int 19 p-values: MWU [T-Test]
Tiger control 316 int 19 v Chimera 316 int 19 p-values: MWU [T-Test]
[1] Tiger control 316 int 19 (N=5) mean (CV)
[2] VSV control 316 int 19 (N=5) mean (CV)
[3] TOBB 316 int 19 (N=5) mean (CV)
[4] PTOBB 316 int 19 (N=5) mean (CV)
[5] Short Chimera 316 int 19 (N=5) mean (CV)
[6] Chimera 316 int 19 (N=5) mean (CV)

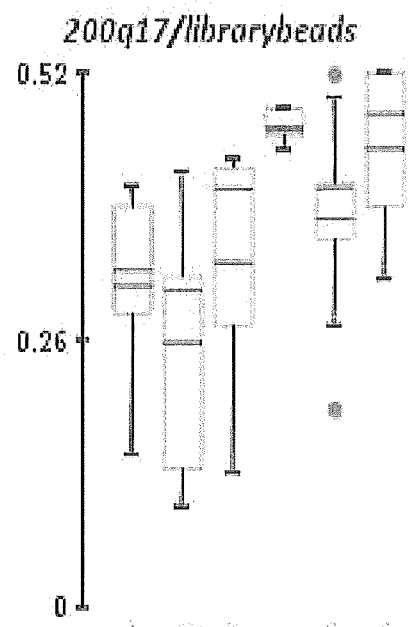

FIG. 10A
*200q17/librarybeads*

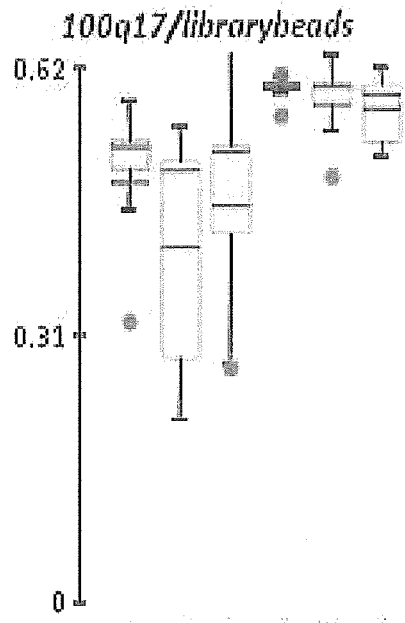

FIG. 10B
*100q17/librarybeads*

0.5476[0.4939]    0.4206[0.3823]
0.6905[0.7705]    0.8413[0.6964]
0.007937[0.02793] 0.007937[0.0561]
0.3095[0.3855]    0.09524[0.09987]
0.1508[0.06174]   0.1508[0.112]

[1] 0.31 (33.3%)   [1] 0.49 (18.8%)
[2] 0.25 (53.2%)   [2] 0.41 (37.2%)
[3] 0.33 (39.3%)   [3] 0.46 (25.0%)
[4] 0.46 (3.8%)    [4] 0.59 (3.1%)
[5] 0.37 (31.5%)   [5] 0.57 (8.3%)
[6] 0.44 (19.9%)   [6] 0.57 (7.8%)

Tiger control 316 int 19 v VSV control 316 int 19 p-values: MWU [T-Test]
Tiger control 316 int 19 v TOBB 316 int 19 p-values: MWU [T-Test]
Tiger control 316 int 19 v PTOBB 316 int 19 p-values: MWU [T-Test]
Tiger control 316 int 19 v Short Chimera 316 int 19 p-values: MWU [T-Test]
Tiger control 316 int 19 v Chimera 316 int 19 p-values: MWU [T-Test]
[1] Tiger control 316 int 19 (N=5) mean (CV)
[2] VSV control 316 int 19 (N=5) mean (CV)
[3] TOBB 316 int 19 (N=5) mean (CV)
[4] PTOBB 316 int 19 (N=5) mean (CV)
[5] Short Chimera 316 int 19 (N=5) mean (CV)
[6] Chimera 316 int 19 (N=5) mean (CV)

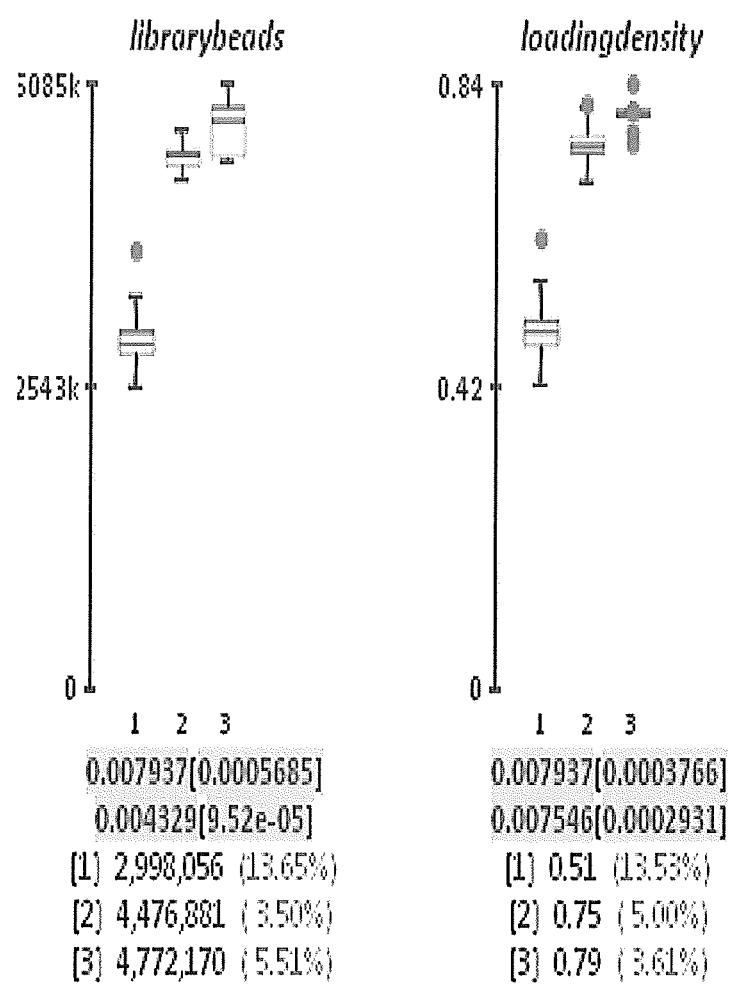

METHODS, COMPOSITIONS AND SYSTEMS FOR SAMPLE DEPOSITION

CROSS-REFERENCE TO RELATED APPLICATION(S)

This application is a continuation of PCT Application No. PCT/US2012/034358, filed Apr. 20, 2012 and entitled "METHODS, COMPOSITIONS AND SYSTEMS FOR SAMPLE DEPOSITION," which claims benefit of U.S. Provisional Application No. 61/477,358, filed Apr. 20, 2011 and entitled "BEAD ARRAY LOADING METHODS AND COMPOSITIONS," claims benefit of U.S. Provisional Application No. 61/546,013, filed Oct. 11, 2011 and entitled "METHODS, COMPOSITIONS AND SYSTEMS FOR SAMPLE DEPOSITION," and claims benefit of U.S. Provisional Application No. 61/585,019, filed Jan. 10, 2012 and entitled "METHODS, COMPOSITIONS AND SYSTEMS FOR SAMPLE DEPOSITION," which applications are incorporated herein by reference in their entirety.

FIELD

The present disclosure is directed towards the field of molecular biology, in particular towards improved loading and retention of samples onto surfaces, including nucleic acid and protein arrays.

BACKGROUND

Various techniques for analyzing biomolecules, such as polynucleotides or proteins, rely on the deposition of an array of particles, each attached to such biomolecules. Exemplary sequencing techniques rely on the deposition of an array of particles including a polynucleotide or copies thereof in an array of wells. In a particular example, the particles or beads can be deposited within the wells to associate the particles or beads with a particular sensor and to provide a local environment in which to analyze the biomolecules. In other examples, an ordered array of particles are deposited on a surface and analyzed without the benefit of wells.

There is a challenge to load samples on a surface in an organized manner, such that each sample does not interfere with another sample on the same surface. There is also a challenge to load closely spaced samples on a surface to form an array. It is desirable to create such arrays for nucleic acid or protein experimentation. In particular, it is desirable to create high-density arrays suitable for sequencing of genomes or for sequencing of low-frequency and rare variant mutations. It would also be desirable to place nucleic acids and in particular, nucleic acids bound to a delivery particle in an organized, tightly packed fashion, for example, to increase sequencing throughput per cycle, to lower customer cost per sequenced base, to run multiple samples in tandem, or to lower the overall amount of reagents used to generate sequencing information from an array. However, as nucleic acid deposition density (or nucleic acid-containing particle density) is increased the likelihood of nucleic acid clumping and nucleic acid stacking on a surface can also increase. Additionally, less than optimal loading conditions can result in one or more nucleic acids (or nucleic acid containing particles) entering the same location on the surface, such as a well, channel, pore or groove, and interfering with downstream data processing. Controlled organization of nucleic acids proteins, or particles and improved loading thereof can also simplify software identification of the nucleic acids or proteins on an array. Unfortunately, when nucleic acids, particles or proteins are stacked or clumped on an array, there can be problems with interrogation for their individual sequence or reporter signals.

In sequencing using delivery particles coated with nucleic acids, the overall throughput in terms of nucleic acid bases sequenced per sequencing run can directly depend on the number of readable delivery particles coated with nucleic acids in a given interrogation area, and generally, the more the better. Additionally, the amount of genetic information processed per run is dependent on the amount of nucleic acid bases sequenced per delivery particle. When delivery particles coated with nucleic acids are dispensed randomly onto an array, a considerable amount of space on the array can be left open. Furthermore, some delivery particles coated with nucleic acids can settle on the array in overlapping fashion, settle among interstitial spaces or stacking with other particles coated with nucleic acids, which can cause difficulties in resolving and interpreting images, signals or sequences of the nucleic acids bound to the delivery particles.

When processing an array containing particles coated with nucleic acids, it can be desirable to have the particles coated with nucleic acids packed as densely as possible to achieve the highest possible throughput. For example, when sequencing particles that include nucleic acids, it can be desirable to have a single nucleic acid sequence at one location on the array, for example, a reaction chamber, and for those locations to be present at a high-density to ensure high sequencing throughput. However, issues may arise for particles coated with nucleic acids such that the ionic field, diffraction circles or spread function is relatively large compared to the actual size of the particles coated with nucleic acids. Packing the particles coated with nucleic acids at a density such that the nucleic acid coated particles are all or mostly all touching each other can result in un-resolvable features, whether these coated particles are randomly arrayed or ordered in a close pack. Thus, improved methods, compositions, systems, apparatuses and kits for depositing samples, particularly particulate samples, onto various array surfaces would be desirable. Improved sequencing throughput of arrays as a result of improved sample loading would be desirable.

SUMMARY

Biomolecule enhanced particles are deposited in an array to facilitate analysis. In an example, methods and devices for performing such methods are utilized to deposit particles attached to polynucleotides into wells of an array associated with an array of sensors.

BRIEF DESCRIPTION OF THE DRAWINGS

The present disclosure will be more fully understood from the following detailed description taken in conjunction with the accompanying drawings, in which:

FIG. 5 and FIG. 6 illustrate exemplary orientations of an array during centrifugation.

FIG. 7 includes a block flow diagram illustrating an exemplary method for depositing biomolecule-enhanced particles into an array.

FIGS. 8A-8C provide sequencing metrics associated with surfaces prepared by various embodiments of the disclosure.

FIGS. 9A-9C provide sequencing metrics associated with surfaces prepared by various embodiments of the disclosure.

FIGS. 10A-10B provide sequencing metrics associated with surfaces prepared by various embodiments of the disclosure.

FIGS. 11A and 11B provide sequencing metrics associated with surfaces prepared by various embodiments of the disclosure.

DETAILED DESCRIPTION

In some embodiments, the disclosure relates generally to methods, compositions, systems, apparatuses and kits for depositing samples, for example, particulate samples, onto one or more surfaces. In some embodiments, the disclosure relates generally to deposition of samples onto a surface to form an array, such as a nucleic acid or protein array. The sample to be deposited can include one or more particles, and the surface can include one or more reaction chambers formed therein. The particles can include one or more biomolecules attached to the particles. The disclosure relates generally to methods and related compositions, kits, systems and apparatuses for depositing a plurality of particles into a plurality of reaction chambers. In some embodiments, the disclosed methods can include forming a particle mixture including a plurality of sample particles. The sample particles optionally have a first average diameter. The particle mixture can optionally further include a plurality of companion particles. In some embodiments, the companion particles have a second average diameter greater than the first average diameter.

Figure 1:
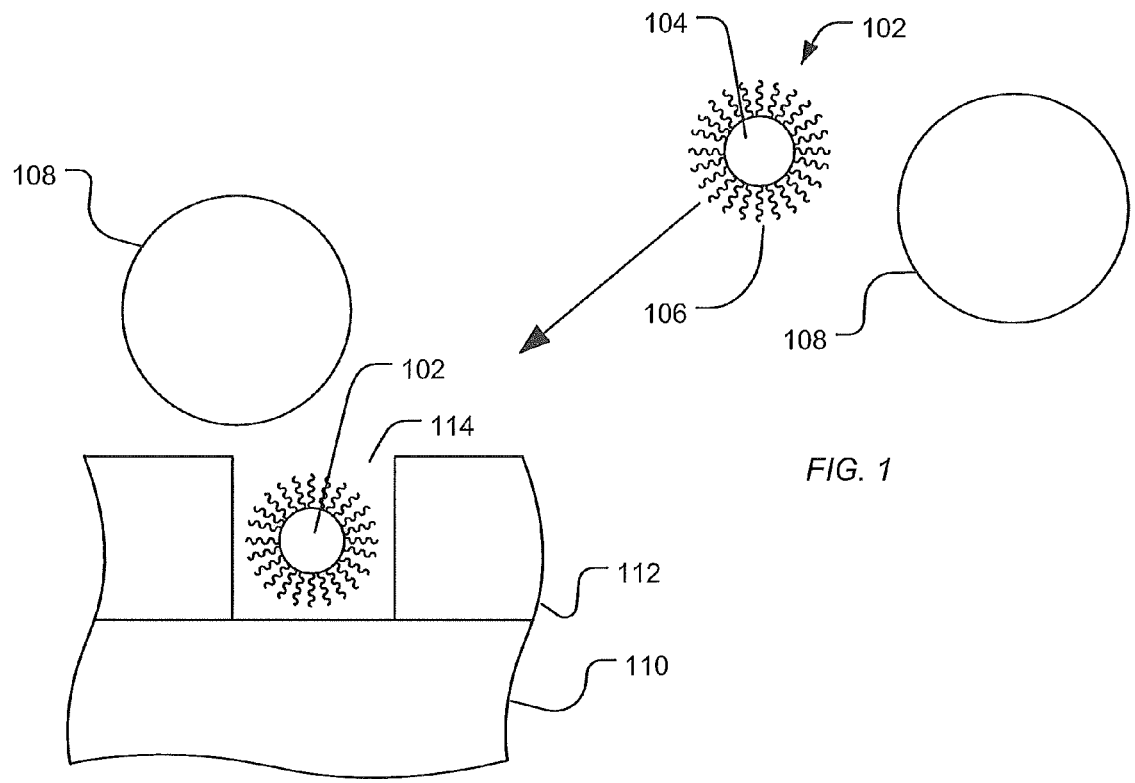
FIG. 1 includes an illustration of an exemplary system for depositing biomolecule-enhanced particles.

As illustrated in FIG. 1, an exemplary biomolecule-enriched particle 102 includes a core 104 and biomolecules 106 attached to the core 104. While the biomolecules 106 are illustrated as being disposed on a surface of the core 104, such biomolecules 106 can be disposed throughout the core 104 and on the surface of the core 104 depending upon the porosity and permeability of the core 104. The biomolecule-enhanced particle 102 can include one or more copies of the biomolecules 106. In particular, the biomolecule-enhanced particle 102 can include at least 1000 copies of the biomolecules 106, such as at least 10,000 copies, at least 1,000,000 copies of the biomolecules 106, or even at least 10 million copies of the biomolecules 106. An exemplary biomolecule 106 can include a protein, a polynucleotide, or a combination thereof. In particular, the biomolecule 106 can be a polynucleotide, such as DNA, RNA, derivatives thereof, or a combination thereof.

The core 104 of the biomolecule-enhanced particles 102 can be formed of various inorganic or organic materials. In particular, the core 104 is an organic material, such as a polymer. For example, the polymer of the core 104 can include a hydrophilic polymer, such as a hydrogel. The polymer can include silicone, polyacrylamide, polyamide, polystyrene, or a combination thereof. An inorganic material can include a glass, a ceramic, or a combination thereof, such as silica, alumina, or a combination thereof.

Optionally, the biomolecule-enhanced particle 102 can be mixed in solution with a companion particle 108. In particular, the companion particle does not include the biomolecule 106. In an example, the companion particle 108 has an effective diameter greater than the biomolecule-enhance particle 102.

The system can include an array including a device layer 110 and a wall structure 112 disposed over the device layer 110 and defining reaction chambers, such as wells 114. The biomolecule-enhanced particle 102 can be deposited within the wells 114. In particular, the effective diameter of the biomolecule-enhanced particle 102 is not greater than the entrance of the well 114. The optional companion particle 108 can have a diameter that is greater than the entrance of the well 114. As such, the companion particle 108 does not fit within the well 114. In a particular example, the companion particle 108 functions to push biomolecule-enhanced particles 102 into wells 114 as the companion particle 108 traverses the surface of the well wall structure 112. Alternatively, biomolecule-enhanced particles 102 can be deposited into wells 114 without the use of companion particles. In particular, the biomolecule-enhanced particles 102 can be driven into wells 114 using centrifugation, vortexing, surface tension, or other means.

Figure 2:
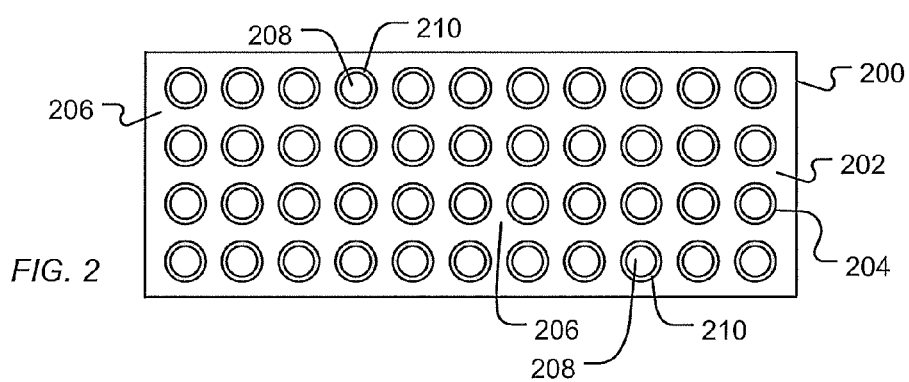
FIG. 2 includes an illustration of an exemplary well array.

As illustrated in FIG. 2, an exemplary system 200 includes a well wall structure 202 defining an array of wells 204 disposed over or operatively coupled to sensor pads of a sensor array. The well wall structure 202 defines an upper surface 206. A lower surface 208 associated with the well is disposed over a sensor pad of the sensor array. The well wall structure 202 defines a sidewall 210 between the upper surface 206 and the lower surface 208. As described above, biomolecule-enhanced particles can be deposited within the wells 204 defined by the well wall structure 202. Such biomolecule-enhanced particles can be analyzed using sensors of the sensor array.

Figure 3:
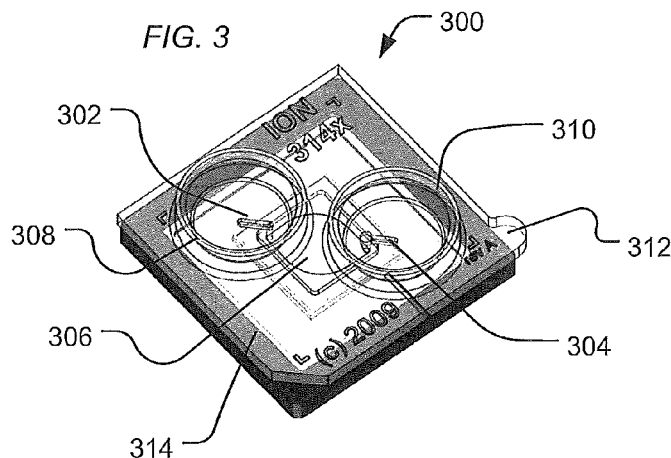
FIG. 3 includes an illustration of an exemplary flow cell in cooperation with an array.

In a particular example, an array, such as a micro well array or a surface array, and associated devices can be cooperatively associated with a cap, defining a flow cell over the array. Further, the cap can define fluid inlet and outlet ports, permitting flow across the array. In particular, FIG. 3 illustrates an exemplary component 300 that includes a cap 314 disposed over the array 306 and defining a flow cell therebetween. The cap 314 defines an inlet port 302 and an efflux port 304. In an example, the efflux port 304 can be larger than the inlet port 302. Fluid can be injected into the inlet port 302 and can flow across the array 306 and out of the efflux port 304. Optionally, the cap 314 defines rims 308 and 310 around the inlet port 302 and efflux port 304, respectively. In use, such rims 308 and 310 can be used to form a seal with engagement structures to prevent fluid leaking onto electronic components. When loading particles onto the array 306, the rims 308 and 310 can define containment areas, pooling liquid samples and preventing such samples from flowing outside of the containment area.

Loading biomolecule-enhanced particles can include applying a portion of a sample to the array and agitating the sample to take advantage of directional forces or surface tension to motivate the biomolecule-enhanced particles into an array, such as wells of the array. The process can be repeated using additional portions of the sample or by reapplying a portion of the sample withdrawn from a flow cell. Optionally, the sample can include companion particles. For example, the sample can be prepared by coupling biomolecules to the biomolecule-enhanced particles, optionally amplifying to make copies of the biomolecules on the particles, and optionally mixing the biomolecule-enhanced particles with companion particles in a solution. In particular, the companion particles can have a diameter significantly greater than the biomolecule-enhanced particle and optionally greater than an entry into the well structures within the array.

Figure 4:
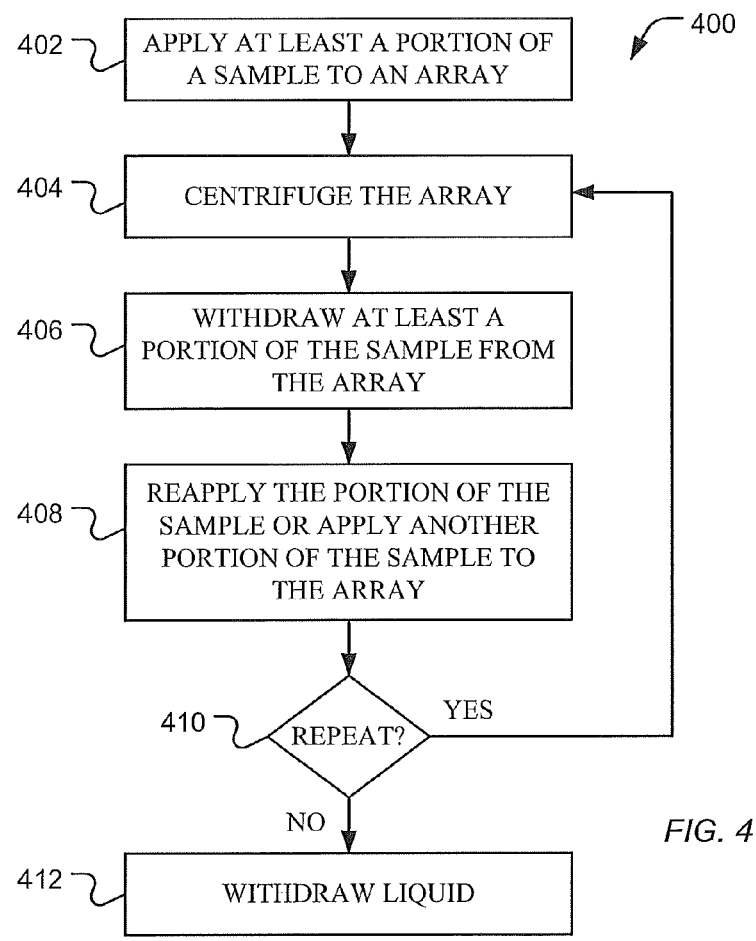
FIG. 4 includes a block flow diagram illustrating an exemplary method for depositing biomolecule-enhanced particles.

For example, as illustrated in FIG. 4, a method 400 includes applying at least a portion of a sample to an array, as illustrated at 402. The sample can include biomolecule-enhanced particles and optionally, can include companion particles. For example, a portion of the sample can be pipetted into a load port of a flow cell defined over an array. Depending on the volume of the sample and the volume of the flow cell, the entire sample can be applied to the flow cell or a portion can be applied to the flow cell. In an example, the load port can be the inlet port 302 or the efflux port 304. For example, particularly when the efflux port 304 is larger than the inlet port 302, the load port can be efflux port. When the load port is the efflux port, a sample outlet port can be the inlet port 302. Alternatively, the outlet port can be the efflux port 304.

As illustrated at 404, the array can be centrifuged. Optionally, the array can be held perpendicular to the plane in which the rotation occurs during centrifugation. Alternatively, the array can be held at an angle relative to the plane within which rotation occurs during centrifugation. In an example, the array can face towards a central point around which rotation occurs. Alternatively, the array can face outward and away from a central point around which rotation occurs.

For example, as illustrated in FIG. 5, an array 504 is positioned within a plane perpendicular to the plane within which rotation 502 occurs during centrifugation. As illustrated in FIG. 5, the array 504 resides within a plane that is parallel to the x and y-coordinates and perpendicular to the radial coordinate, r. As illustrated, the x-coordinate extends into the page and the y-coordinate extends parallel the page. Both x and y-coordinates are orthogonal to r.

Alternatively, as illustrated in FIG. 6, an array 604 can be tilted relative to the plane in which rotation 602 occurs. For example, the array 604 can be rotated around the x-axis to define an angle alpha relative to the radial direction. The angle alpha is generally greater than 0° and less than 180°. In a particular example, the angle alpha is not greater than 90°, such as not greater than 75°, or even not greater than 65°. The angle alpha can be at least 15°, such as at least 30° or even at least 35°.

In both of the examples of FIG. 5 and FIG. 6, a load port can be positioned closer to a lower end of the array (504 or 604) as illustrated and an output port can be positioned closer to a higher end of the array (504 or 604) as illustrated. The reference to lower or higher is relative to the illustrated y-axis. Alternatively, the load port can be positioned higher than the output port. In both examples, the array can optionally face towards a center of the rotation or can alternatively face away from the center rotation. In addition, such orientations can be changed at different steps of the method.

Following centrifugation, at least a portion of the sample can be withdrawn from the array, as illustrated 406. In an example, the portion is withdrawn from an output port. Alternatively, the portion of the sample can be withdrawn using the same port through which the sample or portion of the sample was applied.

As illustrated at 408, a portion of the sample can be reapplied or another portion of the sample can be applied to the array. Optionally, the other portion can be applied prior to drawing a previous portion. For example, the other portion can be applied to the load port and the previous portion displaced by the other portion and exiting the output port can be withdrawn.

As illustrated at 410, the process can be repeated. In particular, portions that are newly applied or reapplied to the array can be centrifuged, as described above and illustrated at 404. In an example, the process can be repeated until the sample is exhausted. Alternatively, the process can be repeated for each new portion at least once, such as at least twice, or even at least 3 times. Optionally, the liquid can be withdrawn from the flow cell, as illustrated at 412, once sample has been applied and centrifuged. In a particular example, the array can be positioned within an instrument and analysis, such as sequencing, can be performed.

In an alternative example, air/liquid interfaces can be utilized to motivate biomolecule-enhanced particles into an array, such as a microwell array. For example, as illustrated in FIG. 7, a method 700 includes creating a foam from at least a portion of the sample, as illustrated at 702. The foam can be created by aspirating gas through the sample. The size of bubbles can be altered using rapid pipetting or other techniques. In particular, the sample includes biomolecule-enhanced particles. The sample may or may not include companion particles.

As illustrated at 704, at least a portion of the foam can be applied to the array. For example, a portion of the foam can be applied to the load port.

The foam can be moved or agitated, for example by vortexing the array, illustrated at 706, or using other techniques such as applying pulses of air pressure to the foam. In an example, vortexing moves the air/liquid interface over the microwell array, facilitating the deposition of the biomolecule-enhanced particles into wells of the array.

Following vortexing, another portion of the foam can be applied to the array, as illustrated at 708. The application of an additional portion of the foam can drive the previously applied portion of the foam through an efflux port. Such used foam can be collected as a waste or can be reapplied during a later step.

As illustrated at 710, the process can be repeated and the applied foam portions can be vortexed with the array, as illustrated at 706. Optionally, once each portion of the foam has been applied to the array, the used portions of foam can be reapplied to the array or can be mixed and reapplied to the array.

Following deposition of the sample, the remaining foam can be flushed out of or withdrawn from the flow cell disposed over the array, as illustrated 712. The component including the array can be positioned within a device for analysis, such as a sequencing device.

In some embodiments, the method can further include contacting the particle mixture with a surface. The surface can include at least one reaction chamber, optionally a plurality of reaction chambers. At least some of the reaction chambers can include an entry. Typically, the entry can permit at least one particle to enter the reaction chamber.

In some embodiments, the reaction chamber entry (or entries), the sample particle and the companion particle can be sized so as to selectively admit only one type of particle (sample or companion) into the reaction chamber, but not the other type. For example, in some embodiments, the average cross-sectional diameter of the reaction chamber entries can be less than the first average diameter of the sample particles, such that at least some of the sample particles can enter the reaction chambers through the entries. In some embodiments, the average cross-sectional diameter of the reaction chamber entries can be greater than the second average diameter of the companion particles, such that at least some of the companion particles cannot enter the reaction chambers through the entries and are thus substantially excluded from the reaction chambers. Alternatively, the average cross-sectional diameter of the reaction chamber entries can be greater than the first average diameter of the sample particles, such that at least some of the sample particles cannot enter the reaction chambers through the entries and are thus substantially excluded from the reaction chambers. Further, the average cross-sectional diameter of the reaction chamber entries can be less than the second average diameter of the companion particles, such that at least some of the companion particles can enter the reaction chambers through the entries.

In some embodiments, the average cross sectional diameter of the entries of the plurality of reaction chambers is greater than the first average diameter of the sample particles. In some embodiments, the average cross sectional diameter of the entries is less than the second average diameter.

In some embodiments, the disclosed methods can further include depositing at least one sample particle into at least one reaction chamber of the array. Optionally, the depositing includes depositing at least one sample particle at an identifiable position on the array.

In some embodiments, the disclosed methods can further include depositing a sample particle of the particle mixture into a percentage of the reaction chambers of the array.

In some embodiments, the percentage of reaction chambers containing a deposited sample particle from the particle mixture can be at least 50%, at least 60%, at least 70%, at least 80%, at least 90%, or greater.

In some embodiments, the percentage of sample particles deposited into one or more reaction chambers on the surface can be increased relative to the percentage of reaction chambers that are filled by a control particle mixture that does not include companion particles. In some embodiments, the percentage increase of reaction chambers containing a deposited sample particle from the particle mixture (as compared to the percentage of reaction chambers containing a deposited sample particle from the control particle mixture) can be at least 10%, at least 20%, or at least 30%. The control particle mixture can include the same total number of sample particles as the particle mixture. The control particle mixture can be identical to the particle mixture except that the control mixture does not contain companion particles. In some embodiments, the volume of the control particle mixture can be the same as the volume of the particle mixture. In some embodiments, the total number or weight of sample particles in the control particle mixture can be the same as the total number or weight of sample particles in the particle mixture.

In some embodiments, the disclosed methods can further include detecting deposition of a sample particle in a reaction chamber of the array. The detecting can include using a sensor, which can optionally be operatively coupled to at least one reaction chamber of the array.

In some embodiments, the disclosed methods can further include correlating the deposition of at least one sample particle in the reaction chamber with improved signal to noise ratio, improved conversion, improved key peak or improved quality of sequencing data In some embodiments, the disclosed methods can be used for nucleic acid sequencing, such as high-throughput next generation sequencing or for protein analysis, such as protein detection or isolation. As outlined herein, the methods are not limited by the source of materials and therefore include all forms of genetic and proteomic samples. For example, the methods can include deposition of a sample particle from a DNA, RNA, genomic DNA, cDNA, mRNA, siRNA, cDNA, lambda DNA, bacterial, viral, eukaryotic or prokaryotic source of genetic material. In some embodiments, the methods can include deposition of a sample particle from a full length protein, truncated protein, N-terminal protein, C-terminal protein, mutant protein, folded protein, protein fragment, purified protein and the like. Additionally, the methods are not limited to the desired application and for example include animal, chimeric or pathogenic sequencing. The methods also include sequencing of samples such as environmental samples, manufacturing samples, contamination detection such as food supply and manufacturer's samples, and forensic samples. In some embodiments, the methods herein can be used in semi-conductor based sequencing technology, such as Ion Torrent™ PGM Sequencing.

In some embodiments, the disclosed methods can further include removing a portion of the particle mixture from the surface to enhance loading.

In some embodiments, the method can include separating one or more companion particles from the surface after at least one sample particle is deposited onto the surface, or into a reaction chamber formed in the surface.

In some embodiments, the companion particles in the particle mixture can facilitate deposition of the sample particles to the surface. The particle mixture can in some embodiments, comprise from about 0.5% by weight to about 90% by weight, 1% by weight to about 60% by weight, 1.5% by weight to about 40% by weight more typically from about 2% by weight to about 20% by weight, of companion particles. The companion particles in the particle mixture can have or include an average diameter that is greater than the average diameter of the sample particles.

In some embodiments, the sample particles deposited onto the surface, or into one or more reaction chambers formed in or on the surface form a monolayer of sample particles.

In some embodiments, the surface can include an array, for example an array of reaction chambers or other structures. In some embodiments, the array can include a plurality of a reaction chambers. At least one of the reaction chambers can optionally be shaped so that it can include no greater than one sample particle at a given time. In some embodiments, at least one of the reaction chambers can be a microwell.

In some embodiments, the sample particles can include one or more nucleic acid molecules attached to a delivery particle. In some embodiments, the delivery particle includes a bead.

In some embodiments, the disclosed methods for loading particles onto a surface can be useful in generating surface arrays of delivery particles including nucleic acid molecules, which can be subjected to suitable methods for sequencing one or more nucleic acid molecules attached to one or more delivery particles.

In some embodiments, the disclosure relates generally to methods (and related compositions, kits, systems and apparatuses) for depositing a plurality of particles into a plurality of reaction chambers. The method includes (a) forming a particle mixture including a plurality of sample particles having a first average diameter and a plurality of companion particles having a second average diameter, and (b) contacting the particle mixture with a surface including a plurality of reaction chambers having entries, wherein the average cross sectional diameter of the entries of the plurality of reaction chambers is greater than the first average diameter but less than the second average diameter. Optionally, the methods can further include depositing at least one sample particle into at least one reaction chamber on the array. The deposition of the at least one sample particle can occur at an identifiable position on the array.

In some embodiments, the companion particles can be inert. In some embodiments, the companion particles can comprise spheres, regular or irregular shaped objects having an average diameter greater than the average cross sectional diameter of the one or more reaction chambers. In some embodiments, a companion particle can include at least two different types of material. In some embodiments, the plurality of companion particles can include at least two different subpopulations of companion particles. For example, the plurality of companion particles can include a first subpopulation of companion particles having a second average diameter and a second subpopulation of companion particles having a third average diameter. In some embodiments, the average diameter of at least one subpopulation of companion particles is greater than the average cross sectional diameter of the entries of the reaction chambers of the surface. For example, the second average diameter, the third average diameter, or both the second and third average diameters can be greater than the average cross sectional diameter of the entries of the one or more reaction chambers.

According to various embodiments, the disclosure relates generally to methods (and related compositions, kits, systems and apparatuses) for increasing signal to noise ratio of an array, comprising: forming a particle mixture including a plurality of sample particles having a first average diameter and a plurality of companion particles having a second average diameter, contacting the particle mixture with an array including a plurality of reaction chambers having entries, wherein the average cross section diameter of the entries of the plurality of reaction chambers is greater than the first average diameter but less than the second average diameter, depositing a sample particle of the particle mixture into a percentage of the reaction chambers, wherein a reaction chamber is operable linked to a sensor, detecting deposition of a sample particle in a reaction chamber, and correlating the deposition of at least one sample particle in the reaction chamber with improved signal to noise ratio, improved conversion, or improved key peak signal.

According to various embodiments, a method for improving loading density of an array is provided that comprises: (a) forming a particle mixture including a plurality of sample particles having a first average diameter and a plurality of companion particles having a second average diameter, and (b) contacting the particle mixture with a surface of an array including a plurality of reaction chambers having entries, wherein the average cross sectional diameter of the entries of the plurality of reaction chambers is greater than the first average diameter but less than the second average diameter, wherein the contacting includes depositing a sample particle of the particle mixture into a percentage of the reaction chambers on the array, and wherein the percentage is increased relative to the percentage of reaction chambers that are filled by a control particle mixture that does not include companion particles.

According to various embodiments, a method for increasing signal to noise ratio of an array is provided, which includes forming a particle mixture including a plurality of sample particles having a first average diameter and a plurality of companion particles having a second average diameter, contacting the particle mixture with an array including a plurality of reaction chambers having entries, wherein the average cross section diameter of the entries of the plurality of reaction chambers is greater than the first average diameter but less than the second average diameter, depositing a sample particle of the particle mixture into a percentage of the reaction chambers, wherein a reaction chamber is operable linked to a sensor, detecting deposition of a sample particle in a reaction chamber, and correlating the deposition of at least one sample particle in the reaction chamber with improved signal to noise ratio, improved conversion, or improved key peak signal.

According to various embodiments, a method of forming an ordered array is provided that comprises forming a particle mixture including a plurality of sample particles having a first average diameter with a plurality of companion particles having a second average diameter, contacting the particle mixture with a surface of the array having a plurality of reaction chambers having entries, wherein the average cross sectional diameter of the entries of the plurality of reaction chambers is greater than the first average diameter but less than the second average diameter, and depositing at least one sample particle into at least one reaction chamber on the array, wherein the deposition of the at least one sample particle is at an identifiable position on the array. In some embodiments, the companion particles can be inert. In some embodiments, the companion particles can comprise spheres, regular or irregular shaped objects having an average diameter greater than the average cross sectional diameter of the one or more reaction chambers. In some embodiments, a companion particle can include at least two different types of material. In some embodiments, a companion particle can include at least two different average diameters, a second average diameter and a third average diameter, wherein the second and third average diameter are both greater than the average cross sectional diameter of the one or more reaction chambers.

In various embodiments, a method is provided for depositing a plurality of particles into a plurality of reaction chambers that comprises: (a) forming a particle mixture including a plurality of sample particles having a first average diameter and a plurality of companion particles having a second average diameter, and (b) contacting the particle mixture with a surface including a plurality of reaction chambers having entries, wherein the average cross sectional diameter of the entries of the plurality of reaction chambers is greater than the first average diameter but less than the second average diameter. In some embodiments, the contacting includes depositing a sample particle of the particle mixture into a percentage of the reaction chambers. In some embodiments, the percentage of reaction chambers containing a deposited sample particle from the particle mixture can be at least 50%, at least 60%, at least 70%, at least 80%, at least 90%, or more. In some embodiments, the percentage of sample particles deposited into one or more reaction chambers on the surface can be increased relative to the percentage of reaction chambers that are filled by a control particle mixture that does not include companion particles. In some embodiments, the control particle mixture includes the same total number of sample particles as the particle mixture. In some embodiments, the control particle mixture can be identical to the particle mixture except that the control mixture does not contain companion particles. In some embodiments, the volume of the control particle mixture can be the same as the volume of the particle mixture. In some embodiments, the total number or weight of sample particles in the control particle mixture can be the same as the total number or weight of sample particles in the particle mixture. In some embodiments, the percentage increase of reaction chambers containing a deposited sample particle from the particle mixture (as compared to the percentage of reaction chambers containing a deposited sample particle from the control particle mixture) can be at least 10%, at least 20%, or at least 30%.

In some embodiments, at least one of the reaction chambers of the surface contains no greater than one sample particle. In some embodiments, when one or more sample particles are deposited in one or more reaction chambers the sample particles can be deposited such that one sample particle is not in direct contact with another sample particle on the surface. In some embodiments, one or more sample particles from the particle mixture deposited in the one or more reaction chambers can be separated such that the sample particles are not touching. In some embodiments, the sample particles of the particle mixture can be deposited at a rate of one sample particle per reaction chamber. In some embodiments, the contacting can include depositing no more than one sample particle in at least one reaction chamber on the surface. In some embodiments, the contacting can include depositing each of at least two sample particles into different reaction chambers.

In some embodiments, the method further comprises separating at least one companion particle from the surface, optionally without dislodging at least one sample particle from at least one reaction chamber. In some embodiments, the separating can include removal of at least one companion particle from the surface using magnetic, centrifugal, gravitational, or other forces that cause at least one of the companion particles to be removed from the surface. In some embodiments, the surface can be flushed with a solution such that one or more companion particles can be separated. In some embodiments, the solution can be a washing solution. In some embodiments, the washing solution can include a detergent. In some embodiments, the separating can include removing at least about 20%, 30%, 40%, 50%, 60%, 70%, 80%, 90%, 95%, or about 99% of the companion particles from the surface. In some embodiments, the separating can include repeated flushing of one or more solutions across the surface until at least 60%, 70%, 80%, 90%, 95%, or more of the companion particles are removed from the surface. In some embodiments, the separating does not substantially affect the number of sample particles in the one or more reaction chambers on the surface. In some embodiments, separating companion particles from the surface dislodges less than 15%, less than 10%, less than 5%, less than 3% of the sample particles deposited in the one or more reaction chambers.

In some embodiments, the method further comprises agitating the particle mixture after contacting the surface. In some embodiments, the agitating can include shaking, tilting, vortexing, spinning, centrifuging, concentrating, pipetting, aspirating, and the like, or other means of associating the sample particles with the companion particles such that the agitating facilitates deposition of the sample particles into one or more reaction chambers on the surface. In some embodiments, the agitating can include one or more of the above techniques or means of associating the sample particles with the companion particles, in any order, or in any combination. In some embodiments, one or more of the techniques or means for associating the sample particles with the companion particles may be repeated or omitted. In some embodiments, the agitating can comprise vortexing, centrifugation and aspirating of the particle mixture contacted with the surface. In some embodiments, agitating can comprise centrifugation, aspirating and pipetting the particle mixture contacted with the surface. In some embodiments, agitating can comprise centrifugation, concentrating and aspirating of the particle mixture contacted with the surface. In some embodiments, agitating can further include removing all, or portions of the particle mixture from the surface and re-applying said portion of the particle mixture to the surface, optionally without dislodging a substantial number of sample particles from the reaction chambers. In some embodiments of the method, agitating can further include removing a volume of the particle mixture from the surface on one or more occasions, optionally without dislodging a substantial number of sample particles from the one or more reaction chambers. While not wishing to be bound by the following theory, it is believed that removing a volume of the particle mixture from the surface decreases the overall volume present on the surface (and in the reaction chambers) at a defined time and consequently increases the likelihood of one or more sample particles being present at the air/aqueous interface on the surface. It is contemplated that a substantial number of sample particles can be deposited in the reaction chambers of the surface through interaction at the aqueous/air interface.

While not wishing to be bound by the following, it is also believed that decreasing the overall volume of the particle mixture present on the surface during agitating can facilitate interaction of the sample particles with the companion particles, and that such frequency of interactions, increases as the volume on the surface or in the reaction chambers decreases. It is also contemplated that in addition to increasing the number of encounters a sample particle can have with one or more companion particles as the particle mixture volume decreases, the probability of one or more sample particles encountering capillary action (for example, when the surface is a channel, pore, nanopore, well or microwell) is increased, thereby facilitating deposition of one or more of the sample particles in the one or more reaction chambers. As such, the methods outlined by the present teachings enhance deposition of sample particles from a particle mixture into one or more reaction chambers on a surface.

In some embodiments, the surface to which the one or more sample particles can be deposited is an array. In some embodiments, the array can be a nucleic acid or protein-based array. In some embodiments, the array can be a sequencing array. In some embodiments, the array can be a detection-based array. In various embodiments of the method, the array can comprise a solid support, a bead array, a slide, a flowcell, a microfluidic array, a nanofluidic array, a semiconductor-based array or a chip. In some embodiments, an array once deposited with one or more sample particles from a particle mixture can be used for nucleic acid sequencing.

In some embodiments of the method, the reaction chamber can comprise a well, channel, groove, pore, nanopore or microwell. The reaction chamber can include one or more entries to through which particles can be introduced into the reaction chamber. Typically, if the reaction chamber includes only one entry, then a particle or other type of sample passes through that entry to enter the reaction chamber. Typically, if the reaction chamber includes multiple entries, then the particle or other type of sample passes through at least one entry of the chamber. Any suitable surface for forming one or more reaction chambers can be used. In some embodiments, the cross sectional average diameter of the one or more reaction chambers, or of the entries of the one or more reaction chambers, is greater than the diameter of a sample particle, but less than the average diameter of a companion particle. In some embodiments, the sample particles of the particle mixture can be deposited into one or more reaction chambers on the surface. In some embodiments, a reaction chamber can include a microwell, U-shaped or V-shaped well. In some embodiments, the reaction chambers on the surface can be spherical, square, rectangular, triangular, rod-like, or hexagonal. In some embodiments, the reaction chamber can be two-sided, three-sided, four-sided, five-sided, six-sided, or more.

In various embodiments, the number of reaction chambers on the surface can be defined, or controlled, by the technology used to create the surface. Any suitable method for creating or preparing reaction chambers on a surface can be used. For example, a surface containing reaction chambers can be prepared using micro-etching. In another example, a surface containing high-densities of reaction chambers can be prepared using semiconductor technology. An exemplary high-density surface containing reaction chambers prepared using semiconductor based technology is an Ion Torrent™ Chip (e.g., Ion 314™, 316™ and 318™ chips, Life Technologies, CA). In the above example, the Ion 314™ chip includes about 1.2 million reaction chambers, the Ion 316™ Chip includes about 6 million reaction chambers, and the Ion 318™ chips includes about 20 million reaction chambers on a single surface. In one embodiment of the method, the number of reaction chambers includes about 1 million to about 5 billion reaction chambers. In one embodiment of the method, the number of reaction chambers can be at least 1 million, at least 6 million, at least 20 million, at least 50 million, at least 150 million, at least 600 million, at least 1 billion, or at least 2.5 billion reaction chambers. In some embodiments, one or more of the reaction chambers can be in contact with, operably linked to, or capacitively coupled to a chemical field effect transistor (chemFET) or an ion-sensitive field-effect transistor (ISFET). Exemplary FET suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In some embodiments of the method, a sample particle of the particle mixture can be a nucleic acid or protein. In some embodiments, a sample particle can be a fragment or portion of a protein, such as the N-terminal or C-terminal portion of one or more proteins. In some embodiments, a sample particle can be one or more nucleic acid molecules or proteins attached to a delivery particle that has an average cross-sectional diameter so as to be deposited into one or more reaction chambers on the surface. In some embodiments, a sample particle can be one or more nucleic acid molecules attached to a bead having an average cross-sectional diameter that is less than the average cross-sectional diameter of the reaction chambers on the surface. In some embodiments, the method for depositing sample particles into a plurality of reaction chambers on the surface can be practiced on a nucleic acid molecule or protein which can be isolated from any source, including: an organism; normal or diseased cells or tissues; body fluids; or archived tissue (e.g., tissue archived in formalin or in paraffin). Nucleic acid molecules can be in any form, including chromosomal, genomic, organellar, methylated, cloned, amplified, DNA, cDNA, RNA, RNA/DNA or synthesized. In some embodiments, a nucleic acid molecule can comprise naturally occurring nucleotides, nucleotide analogs, or both. In some embodiments, a nucleic acid molecule can comprise labeled nucleic acids. Any suitable method for labeling nucleic acids may be used. For example, in some embodiments a label can include a luminescent, photoreactive or fluorescent label. In some embodiments, a label can be attached directly to one or more nucleotides or nucleosides of the nucleic acid molecule, which in turn can be attached to a delivery particle. For example, a nucleic acid molecule can be biotinylated at one end to bind with an avidin-like compound (e.g., streptavidin), acting as a delivery particle.

In some embodiments, the delivery particle to which a nucleic acid molecule can be bound can include any suitable material for attaching nucleic acid molecules to the delivery particle. In some embodiments, a delivery particle can include silica, glass, coated glass, coated polyacrylamide, acrylamide, nylon, plastic, ceramic, porous silicon, polystyrene or a combination thereof. In some embodiments, a delivery particle has an average cross-sectional diameter that is less than the average cross sectional diameter of reaction chambers on the surface. In some embodiments, a delivery particle can include a label, dye, binding moiety, magnet or detectable signal. Delivery particles can be coated with a carboxylic acid compound or an amine compound for attaching nucleic acid molecules. For example delivery particles can be coated with an avidin-like compound (e.g., streptavidin) for binding biotinylated nucleic acid molecules. In some embodiments, delivery particles can have a shape that is spherical, hemispherical, cylindrical, barrel-shaped, toroidal, rod-like, disc-like, conical, triangular, cubical, polygonal, tubular, wire-like or irregular. In some embodiments, a delivery particle can have an iron core, or comprise a hydrogel or agarose (e.g., Sepharose™). In some embodiments, a delivery particle can be paramagnetic. In some embodiments, a delivery particle can have a cavitation or pore, or can include a three-dimensional scaffold. In some embodiments, a delivery particle can be an Ion Sphere™ particle.

In various embodiments of the method, sample particles can include a delivery particle and at least one nucleic acid molecule or a protein. In some embodiments, the particle mixture includes a plurality of sample particles and companion particles having a defined average diameter as compared to the one or more reaction chambers of the surface. In one embodiment, the particle mixture of the method comprises about 80% to about 98% by weight sample particles. In some embodiments, the particle mixture comprises about 2% to about 20% by weight companion particles. In another embodiment, the particle mixture comprises less than 15% companion particles, as determined by the total number of particles in the particle mixture. In another embodiment, the total number of companion particles in the particle mixture is less than 12%, less than 10%, less than 8%, less than 6%, less than 4%, or less than 2% companion particles. In some embodiments, the average cross sectional diameter of a sample particle can be sufficient to deposit one sample particle into a reaction chamber on the surface. In some embodiments of the method, the average diameter of a sample particle in the particle mixture can be at least 5%, 10%, 15%, 20%, 25%, 30%, 35%, or about 40% smaller than the average cross sectional diameter of the entries to the plurality of reaction chambers on the surface. In some embodiments, the reaction chambers on the surface can include a top end and a base, wherein the top end has a smaller average cross sectional diameter than the average cross-sectional diameter of the base of the reaction chambers. In some embodiments, the top end of the reaction chamber can include an entry. In other embodiments, the entry can be located within the base of the reaction chamber. The entry can have an average cross sectional diameter that is greater than the first average diameter of the sample particles but less than the second average diameter of the companion particles.

In various embodiments of the method, a companion particle of the particle mixture can include a bead, and the like. In some embodiments, a companion particle can include silica, glass, coated glass, coated polyacrylamide, acrylamide, nylon, plastic, ceramic, porous silicon, polystyrene, latex or a combination thereof. In some embodiments, a companion particle can be inert. In some embodiments, a companion particle can include a label, dye, binding moiety, magnet or detectable signal. In some embodiments, companion particles can have a shape that is spherical, hemispherical, cylindrical, barrel-shaped, toroidal, rod-like, disc-like, conical, triangular, cubical, polygonal, tubular, wire-like or irregular. In some embodiments, a companion particle can have an iron core, or comprise a hydrogel or agarose (e.g., Sepharose™). In some embodiments, a companion particle can be magnetic or paramagnetic. In some embodiments, a companion particle can have a cavitation or pore, or can include a three-dimensional scaffold. In some embodiments, a companion particle can include coated particles, such as streptavidin coated particles, and the like. In some embodiments, a companion particle can include a surfactant free coating, such as surfactant free blue sulfate or surfactant free yellow green sulfate. In some embodiments, a companion particle can include an ionic or nonionic coating. Any suitable material for preparing a companion particle for use in the disclosed method may be used.

In some embodiments, a companion particle can have an average cross-sectional diameter that is greater than the average cross sectional diameter of at least some of the reaction chambers on the surface. In some embodiments, the average diameter of a companion particle is greater than the average diameter of a sample particle. In some embodiments, a companion particle can comprise at least 2%, 5%, 10%, 20%, 30%, 40%, 50%, 60%, 70%, 80%, 90%, 100%, or more, than the average diameter of a sample particle in a reaction chamber. In some embodiments, a companion particle can include one type of material. For example, a companion particle can include polystyrene. In some embodiments, a companion particle can include two or more types of material. For example, a companion particle can include both silica and iron. In some embodiments, a companion particle having a second average diameter can further include a third average diameter, that is larger than the average cross sectional diameter of the one or more reaction chambers, and is larger than the average diameter of the sample particles having a first average diameter.

In some embodiments, a companion particle can directly facilitate depositing of a sample particle into a reaction chamber by physically contacting a sample particle and moving the sample particle to an entry of a reaction chamber, whereby the entry of the reaction chamber has an average cross sectional diameter that is greater than the average diameter of the sample particle, thereby causing deposition of the sample particle into the reaction chamber. In some embodiments, the depositing of a sample particle into a reaction chamber by a companion particle causes formation of a monolayer of sample particles in the reaction chambers of the surface.

While not wishing to be bound by the following theory, it is believed that a companion particle facilitates depositing of one or more sample particles by physically interacting and moving a sample particle on the surface, thereby optimizing configuration of a sample particle on the surface. It is contemplated herein that a companion particle drives deposition of sample particles into reaction chambers on the surface. For example, when the surface is a microwell, it is believed that companion particles can physically interact with, and move a sample particle of the instant disclosure into a microwell, thereby depositing a sample particle into the reaction chamber. It is also contemplated herein that a companion particle (possessing a greater average diameter than the average diameter of a sample particle) can move a sample particle from interstitial spaces on the surface to a reaction chamber on the surface, thereby enhancing sample loading.

In some embodiments, a method for enhancing loading of a sample to a plurality of reaction chambers is provided comprising, applying to a surface a particle mixture including a plurality of samples particles having a first average diameter and a plurality of companion particles having a second average diameter, contacting the particle mixture with the surface including a plurality of reaction chambers having entries, wherein the average cross sectional diameter of the entries is greater than the first average diameter but less than the second average diameter, and depositing a portion of the sample particles of the particle mixture into a percentage of the reaction chambers on the surface. In some embodiments, after the particle mixture is contacted with the surface, one or more of the companion particles can be separated from the surface. In another embodiment, a portion of the particle mixture contacted with the surface can be removed and re-applied to the surface to facilitate loading of one or more sample particles to the reaction chambers on the surface. In some embodiments, the method further comprises removing one or more unbound sample particles or one or more companion particles from the surface using a wash solution. In some embodiments, a substantial amount of unbound sample particles or companion particles can be removed from the surface using a wash solution. In some embodiments, the wash solution can include one or more salts, detergents or excipients such that the wash solution does not interfere with a sample particle in one or more of the reaction chambers. In some embodiments, the method can further include pre-loading the reaction chambers of the surface with a priming solution comprising an annealing buffer to enhance depositing of a sample particle to a reaction chamber. In some embodiments, the priming solution can include a detergent or an alcohol. In some embodiments, the priming solution can include isopropanol or a non-ionic detergent, an anionic detergent, a zwitterionic detergent, or a combination thereof. In some embodiments, the priming solution can include TWEEN™, TRITON™ or SDS.

In some embodiments, a sample particle in a reaction chamber can be a nucleic acid molecule. In one embodiments, a sample particle in a reaction chamber can be used for one or more sequencing reactions. In some embodiments, the sequencing reaction can include single-stranded or bi-directional (paired-end) sequencing. Any suitable method of sequencing may be used. In some embodiments, the sequencing reaction can identify one or more mutations within the nucleic acid molecule in the reaction chamber. In some embodiments, the method can comprise applying a sequencing polymerase to the particle mixture. In some embodiments, the method can include applying a sequencing primer to the particle mixture. In some embodiments, one or more sample particles can be bound to one or more reaction chambers, wherein the sample particles comprise one or more nucleic acid molecules. In some embodiments, the particle mixture can include sample particles from one or more DNA or nucleic acid origins. In some embodiments, one or more sample particles of the particle mixture can include one or more tissue samples or cells from a single source or individual. In some embodiments, the particle mixture can include one or more tissue or cell samples from at least two sources or individuals. In some embodiments, the particle mixture can include nucleic acids from a multiplex sample. For example, a particle mixture can include sample particles from at least 96, 384, 680, 1000, 3000, 6000, 10000, or more different sources. In some embodiments, the particle mixture can include a sample particle that comprises a nucleic acid molecule having a barcode sequence. In some embodiments, sample particles can include a plurality of nucleic acid molecules attached to a plurality of delivery particles, wherein the nucleic acid molecules contain at least 30%, 40%, 50%, 60%, 70%, 80%, 90%, 95%, 98% or at least 99% homology. In another embodiment, sample particles can include a plurality of nucleic acid molecules attached to delivery particles, wherein the nucleic acid molecules contain substantially no homology. As defined herein, substantially no homology refers to nucleic acid molecules with less than 30% homology. In some embodiments, the sequencing reactions can identify one or more mutations in one or more nucleic acids deposited in a reaction chamber. In some embodiments, the mutations can include deletions, insertions, inversions or mismatches.

In some embodiments, the method further comprises contacting the surface with a solution of control nucleic acid particles that can include known nucleic acid sequences. In some embodiments, the control nucleic acid particles can be included in the particle mixture and contacted with the surface. In some embodiments, one or more of the control nucleic acid particles can be deposited in one or more of the reaction chambers and used for sequencing. In some embodiments, the control nucleic acid particles can be sequenced and used to obtain a baseline or background sequence from one or more of the reaction chambers. In some embodiments, the control nucleic acid particles can include a reference nucleic acid sample such that the reference sample can be compared to the sample particles in the reaction chambers. In some embodiments, the reference sample can be compared to the nucleic acid sequences obtained from the sample particles in the reaction chambers to identify the sequence of the sample particles or identify the present of one or mutations in the sample particles as compared to the reference sample. In some embodiments, the reference sample is a genomic or amplicon sample. In some embodiments, the reference sample is a biological, clinical, agricultural, manufacturing or environmental sample. In some embodiments, the reference sample is a bacterial, viral, fungal, plant, animal or chimeric nucleic acid sample. Any suitable reference sample can be used to obtain a background or reference nucleic acid sequence, using sequencing methods known to those skilled in the art.

In some embodiments, the method further comprises applying a foaming solution to the surface. In some embodiments, the foaming solution can be applied prior to, concurrently with, or after contacting the particle mixture with the surface. In some embodiments, the foaming solution can include polyethylene gycol or polysorbate. In various embodiments of the method, the foaming solution can include one or more detergents. In some embodiments, the detergent can be a non-ionic detergent, an anionic detergent, a zwitterionic detergent, or a combination thereof. In some exemplary embodiments, the detergent can include TWEEN™, TRITON™, BRIJ™, or SDS.

According to various embodiments, a method of improving sample loading is provided that comprises forming a particle mixture including a plurality of sample particles having a first average diameter and a plurality of companion particles having a second average diameter, contacting the particle mixture with a surface including a plurality of reaction chambers having entries, wherein the average cross sectional diameter of the entries of the plurality of reaction chambers is greater than the first average diameter but less than the second average diameter, and wherein the contacting includes depositing a sample particle of the particle mixture into a percentage of reaction chambers, wherein the percentage is increased relative to the percentage of reaction chambers that are filled by a control particle mixture that does not include companion particles.

In some embodiments, the method further comprises separating at least one companion particle from the surface. In another embodiment, the method further comprises priming a reaction chamber of the surface with a priming solution including an annealing buffer so as to facilitate deposition of a sample particle into a reaction chamber. In some embodiments, the reaction chambers of the surface are contained in an array. In some embodiments, the array can be a flow cell, slide, nanofluidic array, or a bead array and the reaction chamber can be a microwell, groove or nanopore. In some embodiments of the method, the number of reaction chambers on the surface can include about 1 million to about 5 billion reaction chambers. In some embodiments, a sample particle of the particle mixture can include a nucleic acid molecule. In some embodiments, a nucleic acid molecule in a reaction chamber can be used in one or more sequencing reactions. In some embodiments, a sequencing reaction can include analyzing the nucleic acid molecule of the sample particle to a reference nucleic acid sequence. In some embodiments, the particle mixture can include one or more control nucleic acid particles. In some embodiments, a control nucleic acid particle can act as an internal control or a positive control to demonstrate that the sequencing process has been completed or is successful. In some embodiments of the method, the method further includes a sequencing polymerase or a sequencing primer can be included in the particle mixture. In some embodiments, a sequencing primer can include a sequence that is complementary to one or more nucleic acid sequences on the one or more sample particles in the reaction chambers. In some embodiments, a sequencing primer can hybridize to a sample particle under appropriate hybridizing conditions. In some embodiments, a sequencing polymerase can include any suitable polymerase sufficient to bind to, or associate with, a nucleic acid molecule attached to a delivery particle in a reaction chamber, so as to promote or facilitate extension of the sequencing primer hybridized to the nucleic acid molecule. In some embodiments, extension of a sequencing primer can include incorporation of a nucleotide and concommant release of a hydrogen atom. In some embodiments, the release of a hydrogen ion during nucleotide incorporation can be associated with the type of nucleotide incorporated and therefore can determine the sequence of the extended sequencing primer.

Provided herein are kits for deposition of a plurality of sample particles into a plurality of reaction chambers on a surface. In some embodiments, the kits relate generally to nucleic acid and protein based arrays. In some embodiments, the kits relate to sequencing of one or more nucleic acids deposited into a reaction chamber of the surface. In some embodiments, kits include any reagent that can be used to contact a particle mixture including a plurality of sample particles and a plurality of companion particles with a surface. In some embodiments, the kits can include any one or more of the following components: a companion particle, a surface, which can optionally include a plurality of reaction chambers, buffers; cations; one or more primers; one or more enzymes; one or more nucleotides; reagents for nucleic acid purification; or reagents for nucleic acid amplification. In some embodiments, kits include any combination of: polymerase(s); ligase(s); endonuclease(s); kinase(s); phosphatase(s); or nuclease(s).

The present teachings will be more fully understood with reference to the following Examples that are intended to illustrate, not limit, the present teachings.

EXAMPLES

Example 1

The following discloses a non-limiting example of a method to prepare an Ion Torrent 314™ Chip (Life Technologies, Part No. 4462923) and method for enhancing nucleic acid loading on the Ion Torrent 314™ Chip for sequencing using an Ion Torrent PGM™ Sequencer (Life Technologies, Part No. 4462917).

Chip Preparation

1. A new Ion Torrent 314™ Chip was obtained and labeled appropriately to identify the experiment.
2. A Chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).

3. The Chip was removed from the PGM™ sequencer and washed with 50 µl, 100% Isopropanol (2-propanol) and then washed with 3× of 50 µL Annealing Buffer (sold as a component of the Ion PGM™ Reagents Kit, (Life Technologies, Part No. 4468994). Here, each washing step entailed a 2 minute spin on a microcentrifuge at 14,000 rpm.

4. A final rinse of the Chip was performed using 50 µL of 50% Annealing buffer.

It is preferred that when the Chip is not in the PGM™ Sequencer and clamped in position, that a dummy chip is loaded into the PGM™ sequencer to prevent air pockets from forming due to back flow in the squid lines.

The Proceeding steps required the preparation of nucleic-acid loaded beads (here, Ion Sphere Particles loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading 1. 10 million DNA-loaded ISPs or half a plate of ISPs prepared using the Ion Xpress™ Template Kit were transferred into a 200 µl, PCR tube and 1 µl of Ion Sphere™ Test Fragments (sold as a component of the Ion Control Material Kit, Life Technologies, Part No. 4466465) were added. If the DNA-loaded ISPs are in excess of 50 µL, Annealing Buffer (sold as a component of the Ion PGM™ Reagents Kit, (Life Technologies, Part No. 4468994) was added up to ~150 µL and centrifuged once to concentrate. The supernatant was removed to a volume of 25 µl.

2. The DNA-loaded ISPs were washed by filling the sample tube with 150 µL Annealing Buffer and gently mixed by stirring with the tip of a pipette.

3. The sample containing the DNA-loaded ISPs of step 2 were centrifuged for 2 minutes at a minimum of 15000 rcf. The supernatant was discarded, except for a final volume of 5 µL. The 5 µl, volume was mixed by repeated pipetting.

4. 6 µL of Sequencing Primer (sold as a component of the Ion Sequencing Reagents Kit, (Life Technologies, Part No. 4468995) was added to the 5 µL, volume of step 3. If the volume of step 3 is less than 5 µL, the final volume is adjusted by adding Annealing Buffer to a final volume of 11 µL. If adjustment is required, mix the sample well by pipetting.

5. The sample of step 4 was run on the following hybridization program on a thermocycler (for example a "QuickHyb Program") with the following temperature profile:

95° C., for 2 minutes, followed by 37° C., for 2 minutes.

6. 1 µL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes.

During Incubation:

7. A solution (30 µl) containing companion particles (1.5 million) (here, SOLiD EZ Bead 6 um polystyrene beads) was transferred into a 1.5 ml PCR tube, to which 500 ul of 50% Annealing Buffer was added. The solution was vortexed and centrifuged for 2 minutes at a minimum of 15000 rcf. The supernatant was completely removed carefully so as not to disturb the particle pellet.

8. Once the incubation period was complete, the mixture of step 6 (~12 µL) was added to the tube containing companion particles (step 7). The sample was mixed using a pipette at least 10 times.

9. The sample was then sonicated for 10 seconds. Droplets may be deposited on the interior wall of the tube. If this occurs, collect the liquid into one pool by a brief (1-2 seconds) spin in a picocentrifuge and then briefly mix with the tip of a pipette.

10. With the Chip on a flat surface, 6 µL, of the sample (from step 9) was applied to the loading port (large port) of the Chip, dialing down the pipette to gently and slowly deposit the sample into the Chip. A good speed is about 1 µL, every second. Residual liquid was removed from the outlet port.

11. The Chip was then centrifuged at room temperature for 1 minute.

12. Using a pipette, 5 µL, of the applied sample was removed from the Chip (at the outlet port) and re-applied to the Chip (via the loading port), 5 times.

13. The Chip was then centrifuged at room temperature for 30-60 seconds.

14. Steps 12 and 13 were repeated once.

15. All liquid was removed gently from the Chip.

16. Steps 10-15 were repeated using the second half of the sample from step 9.

17. The Chip was then washed 4 times with 50 ul of 50% Annealing Buffer to remove companion particles or unbound ISPs before inserting Chip into PGM™ Sequencer.

18. A PGM™ run was performed essentially according to the protocols provided in the Ion Sequencing Kit User Guide v2.0 (Life Technologies, Part No. 4468997), under the heading "Ion 314™ Chip—Begin the Experiment".

Example 2

The following discloses a non-limiting example of a method to prepare an Ion Torrent 316™ Chip (Life Technologies, Part No. 4469496) and method for enhancing nucleic acid loading on the Ion Torrent 316™ Chip using an Ion Torrent PGM™ Sequencer (Life Technologies, Part No. 4462917).

Chip Preparation

1. A new Ion Torrent 316™ Chip was obtained and labeled appropriately to identify the experiment.

2. A Chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).

3. The Chip was removed from the PGM™ sequencer and washed with 100 µL 100% Isopropanol (2-propanol) and then washed with 3× of 100 µL Annealing Buffer (sold as a component of the Ion PGM™ Reagents Kit, (Life Technologies, Part No. 4468994). Here, each washing step entailed a 2 minute spin on a microcentrifuge at 14,000 rpm.

4. A final rinse of the Chip was performed using 100 µL of 50% Annealing buffer.

It is preferred that when the Chip is not in the PGM™ Sequencer and clamped in position, that a dummy chip is loaded into the PGM™ sequencer to prevent air pockets from forming due to back flow in the squid lines.

The Proceeding steps required the preparation of nucleic-acid loaded beads (here, Ion Sphere Particles loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading 1. 20 million DNA-loaded ISPs or one full plate of ISPs prepared using the Ion Xpress™ Template Kit were transferred into a 200 µL PCR tube and 2 µL Ion Sphere™ Test Fragments from the Ion Control Material Kit (Life Technologies, Part No. 4466465) were added. If the DNA-loaded ISPs are in excess of 50 µL, Annealing Buffer (sold as a component of the Ion PGM™ Reagents Kit, (Life Technologies, Part No. 4468994) was added up to ~150 µL and centrifuged once to concentrate. The supernatant was removed to a volume of 25 µl.
2. The DNA-loaded ISPs were washed by filling the sample tube with 150 µL Annealing Buffer and gently mixed using the tip of pipette.
3. The sample containing the DNA-loaded ISPs of step 2 were centrifuged for 2 minutes at a minimum of 15000 rcf. The supernatant was discarded, except for a final volume of 15 µL. The 15 µL volume was mixed by repeated pipetting.
4. 12 µL of Sequencing Primer (sold as a component of the Ion Sequencing Reagents Kit, (Life Technologies, Part No. 4468995) was added to the 15 µL volume of step 3. If the volume of step 3 is less than 15 µL, the final volume is adjusted by adding Annealing Buffer to a final volume of 27 µL. If adjustment is required, mix the sample well by pipetting.
5. The sample of step 4 was run on the following hybridization program on a thermocycler (for example a "QuickHyb Program") with the following temperature profile:
95° C., for 2 minutes, followed by 37° C., for 2 minutes.
6. 3 µL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes.

During Incubation:
7. A solution (70 µL) containing companion particles (3.5 million) (here, SOLiD EZ Bead 6 um polystyrene beads) was transferred into a 1.5 ml PCR tube, to which 500 µL of 50% Annealing Buffer was added. The solution was vortexed and centrifuged for 2 minutes at a minimum of 15000 rcf. The supernatant was removed carefully so as not to disturb particle pellet and resuspended in 30 µL 50% Annealing buffer.
8. Once the incubation period was complete, the mixture of step 6 (~30 µL) was added to the tube containing 30 µL of companion particles (step 7).
9. The sample was sonicated for 10 seconds. Droplets may be deposited on the interior wall of the tube. If this occurs, collect the liquid into one pool by a brief (1-2 seconds) spin in a picocentrifuge and then briefly mix the sample using the tip of a pipette.
10. With the Chip on a flat surface, 30 µL of the sample (from step 9) was applied to the loading port (large port) of the Chip, dialing down the pipette to gently and slowly deposit the sample into the Chip. A good speed is about 1 µL every second. Residual liquid was removed from the outlet.
11. The Chip was then centrifuged at room temperature for 1 minute.
12. Using a pipette, 25 µL of the applied sample was removed from the Chip (via the outlet port) and re-applied to the Chip (via the loading port), 5 times.
13. The Chip was then centrifuged at room temperature for 30-60 seconds.
14. Steps 12 and 13 were repeated once.
15. All liquid was removed gently from the Chip.
16. Steps 10-15 were repeated using the second half of the sample from step 9.
17. The Chip was then washed 4 times with 50 µL of 50% Annealing Buffer to remove companion particles and unbound ISPs before inserting Chip into PGM™ Sequencer.
18. A PGM™ run was performed essentially according to the protocols provided in the Ion Sequencing Kit User Guide v2.0 (Life Technologies, Part No. 4468997), under the heading "Ion 316™ Chip—Begin the Experiment".

Example 3

The following discloses a non-limiting example of a method to prepare an Ion Torrent 318™ Chip (Life Technologies) and method for enhancing sample loading on the Ion Torrent 318™ Chip using an Ion Torrent PGM™ Sequencer (Life Technologies, Part No. 4462917).

Chip Preparation

1. A new Ion Torrent 318™ Chip was obtained and labeled appropriately to identify the experiment.
2. A Chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).
3. The Chip was removed from the PGM™ sequencer and washed with 100 µL 100% Isopropanol (2-propanol) and then washed with 3× of 100 µL Annealing Buffer (sold as a component of the Ion PGM™ Reagents Kit, (Life Technologies, Part No. 4468994). Here, each washing step entailed a 2 minute spin on a microcentrifuge at 14,000 rpm.
4. A final rinse of the Chip was performed using 100 µL of 50% Annealing buffer.

It is preferred that when the Chip is not in the PGM™ Sequencer and clamped in position, that a dummy chip is loaded into the PGM™ sequencer to prevent air pockets from forming due to back flow in the squid lines.

The Proceeding steps required the preparation of nucleic-acid loaded beads (here, Ion Sphere Particles loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 30 million DNA-loaded ISPs or one full plate of ISPs prepared using the Ion Xpress™ Template Kit were transferred into a 200 µL PCR tube and 2 µL Ion Sphere™ Test Fragments from the Ion Control Material Kit (Life Technologies, Part No. 4466465) were added. If the DNA-loaded ISPs are in excess of 50 Annealing Buffer (sold as a component of the Ion PGM™ Reagents Kit, (Life Technologies, Part No. 4468994) was added up to ~150 µL and centrifuged once to concentrate. The supernatant was removed to a volume of 250.
2. The DNA-loaded ISPs were washed by filling the sample tube with 150 µL Annealing Buffer and gently mixed with the tip of a pipette.

3. The sample containing the DNA-loaded ISPs of step 2 were centrifuged for 2 minutes at a minimum of 15000 rcf. The supernatant was discarded, except for a final volume of 15 μL. The 15 μL volume was mixed by repeated pipetting.

4. 12 μL of Sequencing Primer (sold as a component of the Ion Sequencing Reagents Kit, (Life Technologies, Part No. 4468995) was added to the 15 μL volume of step 3. If the volume of step 3 is less than 15 μL, the final volume is adjusted by adding Annealing Buffer to a final volume of 27 μL. If adjustment is required, mix the sample well by pipetting.

5. The sample of step 4 was run on the following hybridization program on a thermocycler (for example a "QuickHyb Program") with the following temperature profile:

95° C., for 2 minutes, followed by 37° C., for 2 minutes.

6. 3 μL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes.

During Incubation:

7. A solution (100 μL) containing companion particles (5 million) (here, SOLiD EZ Bead 6 um polystyrene beads) was transferred into a 1.5 ml PCR tube, to which 500 μL of 50% Annealing Buffer was added. The solution was vortexed and centrifuged for 2 minutes at a minimum of 15000 rcf. The supernatant was removed carefully so as not to disturb particle pellet and resuspended in 30 μL 50% Annealing buffer.

8. Once the incubation period was complete, the mixture of step 6 (~30 μL) was added to the tube containing 30 μL of companion particles (step 7).

9. The sample was sonicated for 10 seconds. Droplets may be deposited on the interior wall of the tube. If this occurs, collect the liquid into one pool by a brief (1-2 seconds) spin in a picocentrifuge and then briefly mixed with the tip of a pipette.

10. With the Chip on a flat surface, 30 μL of the sample (from step 9) was applied to the loading port (large port) of the Chip, dialing down the pipette to gently and slowly deposit the sample into the Chip. A good speed is about 1 μL every second. Residual liquid was removed from the outlet.

11. The Chip was then centrifuged at room temperature for 1 minute.

12. Using a pipette, 25 μL of the applied sample was removed from the Chip and re-applied to the Chip (via the loading port), 5 times.

13. The Chip was then centrifuged at room temperature for 30-60 seconds.

14. Steps 12 and 13 were repeated once.

15. All liquid was removed gently from the Chip.

16. Steps 10-15 were repeated using the second half of the sample from step 9.

17. The Chip was then washed 4 times with 50 μL of 50% Annealing Buffer to remove companion particles and unbound ISPs before inserting Chip into PGM™ Sequencer.

18. A PGM™ run was performed essentially according to the protocols provided in the Ion Sequencing Kit User Guide v2.0 (Life Technologies, Part No. 4468997).

Example 4

The following discloses another non-limiting example of a method to prepare an Ion Torrent 316™ Chip (Life Technologies, Part No. 4469496) and method for enhancing sample loading on the Ion Torrent 316™ Chip using an Ion Torrent PGM™ Sequencer (Life Technologies, Part No. 4462917).

Chip Preparation

1. A new Ion Torrent 316™ Chip was obtained and labeled appropriately to identify the experiment.

2. A Chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).

3. The Chip was removed from the PGM™ sequencer and washed with 100 μL 100% Isopropanol (2-propanol) and then washed with 3× of 100 μL Annealing Buffer (sold as a component of the Ion PGM™ Reagents Kit, (Life Technologies, Part No. 4468994). Here, each washing step entailed a 2 minute spin on a microcentrifuge at 14,000 rpm.

4. All residual fluid was removed from the Chip. For example, by tilting the chip such that any remaining fluid flows to the outlet port where it was removed using a pipette.

It is preferred that when the Chip is not in the PGM™ Sequencer and clamped in position, that a dummy chip is loaded into the PGM™ sequencer to prevent air pockets from forming due to back flow in the squid lines.

The proceeding steps required the preparation of nucleic-acid loaded beads (here, Ion Sphere Particles loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 20 million DNA-loaded ISPs or one full plate of ISPs prepared using the Ion Xpress™ Template Kit were transferred into a 200 μL PCR tube and 2 μL Ion Sphere™ Test Fragments from the Ion Control Material Kit (Life Technologies, Part No. 4466465) were added. If the DNA-loaded ISPs are in excess of 50 Annealing Buffer (sold as a component of the Ion PGM™ Reagents Kit, (Life Technologies, Part No. 4468994) was added up to ~150 μL and centrifuged once to concentrate. The supernatant was removed to a volume of 250.

2. The DNA-loaded ISPs were washed by filling the sample tube with 150 μL Annealing Buffer and gently mixed with the tip of a pipette.

3. The sample containing the DNA-loaded ISPs of step 2 were centrifuged for 2 minutes at a minimum of 15000 rcf. The supernatant was discarded, except for a final volume of 15 μL. The 15 μL volume was mixed by repeated pipetting.

4. 12 μL of Sequencing Primer (sold as a component of the Ion Sequencing Reagents Kit, (Life Technologies, Part No. 4468995) was added to the 15 μL volume of step 3. If the volume of step 3 is less than 15 the final volume is adjusted by adding Annealing Buffer to a final volume of 27 μL. If adjustment is required, mix the sample well by pipetting.

5. The sample of step 4 was run on the following hybridization program on a thermocycler (for example a "QuickHyb Program") with the following temperature profile:

95° C., for 2 minutes, followed by 37° C., for 2 minutes.

6. 3 μL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes.

During Incubation:
7. A solution (70 μL) containing companion particles (3.5 million) (here, SOLiD EZ Bead 6 um polystyrene beads) was transferred into a 1.5 ml PCR tube, to which 500 μL of annealing buffer was added. The solution was vortexed and centrifuged for 2 minutes at a minimum of 15000 rcf. The supernatant was removed carefully so as not to disturb particle pellet and resuspended in 30 μL Annealing buffer.
8. Once the incubation period was complete, the mixture of step 6 (~30 μL) was added to the tube containing 30 μL of companion particles (step 7).
9. The sample was sonicated for 10 seconds. Droplets may be deposited on the interior wall of the tube. If this occurs, collect the liquid into one pool by a brief (1-2 seconds) spin in a picocentrifuge and then briefly mixed using the tip of a pipette.
10. With the Chip on a flat surface, 30 μL of the sample (from step 9) was applied to the loading port (large port) of the Chip, dialing down the pipette to gently and slowly deposit the sample into the Chip. A good speed is about 1 μL every second. Residual liquid was removed from the outlet.
11. Small covers were placed over each of the Chip ports.
12. The Chip was then centrifuged at room temperature for 1 minute.
13. The Chip was then subjected to four rounds of vortexing and centrifugation under the following conditions: Vortex in IKA MS3 Shaker at 2000 rpm for 20 seconds, followed by centrifugation for 20 seconds.
14. The covers were removed from the ports of the Chip and all liquid was removed from the Chip.
15. Steps 10-14 were repeated with the second half of the sample from step 9.
16. The Chip was then washed 4 times with 50 μL of 50% Annealing Buffer to remove companion particles or unbound ISPs before inserting Chip into PGM™ Sequencer.
17. A PGM™ run was performed essentially according to the protocols provided in the Ion Sequencing Kit User Guide v2.0 (Life Technologies, Part No. 4468997).

Example 5

The following discloses another non-limiting example of a method to prepare an Ion Torrent 316™ Chip (Life Technologies, Part No. 4469496) and method for enhancing sample loading on the Ion Torrent 316™ Chip using an Ion Torrent PGM™ Sequencer (Life Technologies, Part No. 4462917).
Chip Preparation
1. A new Ion Torrent 316™ Chip was obtained and labeled appropriately to identify the experiment.
2. A Chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).
3. The Chip was removed from the PGM™ sequencer and washed with 100 μL 100% Isopropanol (2-propanol) and then washed with 3× of 100 μL Annealing Buffer (sold as a component of the Ion PGM™ Reagents Kit, (Life Technologies, Part No. 4468994). Here, each washing step entailed a 2 minute spin on a microcentrifuge at 14,000 rpm.
4. All residual fluid was removed from the Chip. For example, by tilting the chip such that any remaining fluid flows to the outlet port where it was removed using a pipette.

It is preferred that when the Chip is not in the PGM™ Sequencer and clamped in position, that a dummy chip is loaded into the PGM™ sequencer to prevent air pockets from forming due to back flow in the squid lines.

The proceeding steps required the preparation of nucleic-acid loaded beads (here, Ion Sphere Particles loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.
Enhanced Nucleic Acid Loading (ISPs)
1. 20 million DNA-loaded ISPs or a full plate of ISPs prepared using the Ion Xpress™ Template Kit were transferred into a 200 μL PCR tube and 2 μL Ion Sphere™ Test Fragments from the Ion Control Material Kit (Life Technologies, Part No. 4466465) were added. If the DNA-loaded ISPs are in excess of 50 μL, Annealing Buffer (sold as a component of the Ion PGM™ Reagents Kit, (Life Technologies, Part No. 4468994) was added up to ~150 μL and centrifuged once to concentrate. The supernatant was removed to a volume of 25 μl.
2. The DNA-loaded ISPs were washed by filling the sample tube with 150 μL Annealing Buffer and gently mixed with the tip of a pipette.
3. The sample containing the DNA-loaded ISPs of step 2 were centrifuged for 2 minutes at a minimum of 15000 rcf. The supernatant was discarded, except for a final volume of 15 μL. The 15 μL volume was mixed by repeated pipetting.
4. 12 μL of Sequencing Primer (sold as a component of the Ion Sequencing Reagents Kit, (Life Technologies, Part No. 4468995) was added to the 15 μL volume of step 3. If the volume of step 3 is less than 15 μL, the final volume is adjusted by adding Annealing Buffer to a final volume of 27 μL. If adjustment is required, mix the sample well by pipetting.
5. The sample of step 4 was run on the following hybridization program on a thermocycler (for example a "QuickHyb Program") with the following temperature profile:
  95° C., for 2 minutes, followed by 37° C., for 2 minutes.
6. 3 μL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes.
During Incubation:
7. A solution (70 μL) containing companion particles (3.5 million) (here, SOLiD EZ Bead 6 um polystyrene beads) was transferred into a 1.5 ml PCR tube, to which 500 μL of Annealing buffer was added. The solution was vortexed and centrifuged for 2 minutes at a minimum of 15000 rcf. The supernatant was removed carefully so as not to disturb the particle pellet and resuspended in 30 μL Annealing buffer.
8. Once the incubation period was complete, the mixture of step 6 (~30 μL) was added to the tube containing 30 μL of companion particles (step 7).
9. The sample was sonicated for 10 seconds. Droplets may be deposited on the interior wall of the tube. If this occurs, collect the liquid into one pool by a brief (1-2 seconds) spin in a picocentrifuge and then briefly mixed using the tip of a pipette.
10. With the Chip on a flat surface, 30 μL of the sample (from step 9) was applied to the loading port (large port) of the Chip, dialing down the pipette to gently and slowly deposit the sample into the Chip. A good speed is about 1 µL every second. Residual liquid was removed from the outlet.

11. Small covers were placed over each of the Chip ports.

12. The Chip was then centrifuged at room temperature for 1 minute.

13. The Chip was then subjected to two rounds of vortexing and centrifugation under the following conditions: Vortex in IKA MS3 Shaker at 2000 rpm for 20 seconds, followed by centrifugation for 20 seconds.

14. The covers were removed from the ports of the Chip and all residual fluid was removed from the Chip.

15. Steps 10-14 were repeated with the second half of the sample from step 9.

16. The Chip was then washed 4 times with 50 µL of 50% Annealing Buffer to remove companion particles and unbound ISPs before inserting Chip into PGM™ Sequencer.

17. A PGM™ run was performed essentially according to the protocols provided in the Ion Sequencing Kit User Guide v2.0 (Life Technologies, Part No. 4468997).

Example 6

FIGS. 8A-8C show data obtained using methods of the present disclosure.

FIG. 8A shows the number of 100 base pair read lengths as rated by quality scores of Q17.

FIG. 8B shows the number of 200 base pair read lengths as rated by quality scores of Q17.

FIG. 8C shows the total number of bases from a single run having a quality score of Q17.

Each of the above criteria was tested using six experimental conditions [1]-[6]. Experiments [1] and [2] refer to testing conditions in the absence of companion particles. Experiments [3]-[6] refer to testing conditions in the presence of companion particles. Experiment [3] TOBB, [4] PTOBB (Example 2, herein), [5] Short Chimera (Example 5, herein) and [6] Chimera (Example 4, herein) refer to loading of a nucleic acid array using the methods disclosed herein. Specifically, experiments [3]-[6] involve a different attaching step(s) and include one or more of the techniques disclosed herein to attach nucleic acid bound particles to the array.

Experiments [3]-[6] that included companion particles, were observed to result in an increase in the number of reads (FIGS. 8A and 8B) or total throughput (FIG. 8C) as compared to non-companion particle based arrays. Additionally, the mean length of each read with a Q17 score was found to be longer for experiments including companion particles as compared to non-companion particle counterparts (FIG. 9B). Furthermore, the signal to noise ratio (FIG. 9C) improved when using companion particles on an array, as compared to non-companion particle arrays. In each figure, the numbers in parenthesis corresponds to the standard deviation of the five independent experiments (n=5).

FIGS. 10A and 10B provide data from arrays prepared using companion particles (experiments [3]-[6]), as compared to arrays prepared in the absence of companion particles (experiments [1] and [2]). As can be seen from the data, experiments [3]-[6] were generally observed to generate higher ratios, less standard derivation (indicative of more readable and greater read lengths of nucleic acids bound to the array), as compared to non-companion particle based arrays.

Example 7

The following discloses another non-limiting example of a method for enhancing sample loading on the Ion Torrent 316™ Chip using an Ion Torrent PGM™ Sequencer (Life Technologies, Part No. 4462917).

The proceeding steps required the preparation of nucleic-acid loaded beads (here, Ion Sphere Particles loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 30 million DNA-loaded ISPs or a full plate of ISPs prepared using the Ion Xpress™ Template Kit were transferred into a 200 µL PCR tube and 2 µL Ion Sphere™ Test Fragments from the Ion Control Material Kit (Life Technologies, Part No. 4466465) were added. If the DNA-loaded ISPs are in excess of 50 µL, Annealing Buffer (sold as a component of the Ion PGM™ Reagents Kit, (Life Technologies, Part No. 4468994) was added up to ~150 µL and centrifuged once to concentrate. The supernatant was removed to a volume of 12 µl.

2. 12 µL of Sequencing Primer (sold as a component of the Ion Sequencing Reagents Kit, (Life Technologies, Part No. 4468995) was added to the 12 µL volume of step 1.

4. The sample of step 3 was run on the following hybridization program on a thermocycler (for example a "QuickHyb Program") with the following temperature profile:

95° C., for 2 minutes, followed by 37° C., for 2 minutes.

5. 6 µL of foaming solution (10% Triton-X100 in annealing buffer) was added to the sample of step 4 and mixed.

6. The sample of step 5 was mixed to create foam as follows: air bubbles were injected into the sample of step 5 using a pipette tip, with repeated pipetting (up and down) for about 15 seconds to create a homogenous consistency of small air bubbles. If useful to obtain a consistency of small air bubbles, this step was repeated.

7. 40 µL of the foam created in step 6, was applied to the Chip and centrifuged at 3000 rpm for 2-3 minutes. Any excess solution in the outlet port was discarded.

8. Another 30 µL of the foam created in step 6, was applied to the Chip and centrifuged at 3000 rpm for 2-3 minutes. Any excess solution in the outlet port was discarded.

9. Steps 7 and 8 were repeated with the remaining foam created in step 6.

10. After all the foam created in step 6 was applied to the Chip, the chip was flushed with 100 µL of 100% isopropanol and twice flushed with 100 µL of annealing buffer.

11. 3 µL of Sequencing Polymerase (sold as a component of the Ion Sequencing Reagents Kit, (Life Technologies, Part No. 4468995) was added to 30 µL of annealing buffer and mixed slowly.

11. With the Chip on a flat surface, the sample (from step 11) was applied to the loading port (large port) of the Chip, dialing down the pipette to gently and slowly deposit the sample into the Chip.

12. The Chip was then incubated at room temperature for 5 minutes.

13. The Chip was then inserted into the PGM™ Sequencer and a PGM™ run was performed essentially according to the protocols provided in the Ion Sequencing Kit User Guide v2.0 (Life Technologies, Part No. 4468997).

Example 8

The following discloses a non-limiting example of a method to prepare an Ion Torrent 314™ Chip (Life Technologies, Part No. 4462923) and method for enhancing nucleic acid loading on the Ion Torrent 314™ Chip for sequencing using an Ion Torrent PGM™ Sequencer (Life Technologies, Part No. 4462917).

Chip Preparation

1. A new Ion Torrent 314™ Chip was obtained and labeled appropriately to identify the experiment.
2. A chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).
3. The Chip was removed from the PGM™ sequencer and washed with 100 μL 100% Isopropanol (2-propanol) and then washed with 3× of 100 μL Annealing Buffer (sold as a component of the Ion PGM™ Reagents Kit, (Life Technologies, Part No. 4468994). Here, each washing step entailed a 2 minute spin on a microcentrifuge at 14,000 rpm (16873 rcf).

The proceeding steps required the preparation of nucleic-acid loaded beads (here, Ion Sphere Particles (ISPs) loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 10 million DNA-loaded ISPs or a half plate of ISPs prepared using the Ion Xpress™ Template Kit were transferred into a 200 μL PCR tube and 2 μL Ion Sphere™ Test Fragments from the Ion Control Material Kit (Life Technologies, Part No. 4466465) were added. If the DNA-loaded ISPs are in excess of 50 μL, Annealing Buffer (sold as a component of the Ion PGM™ Reagents Kit, (Life Technologies, Part No. 4468994) was added up to ~150 μL and centrifuged once to concentrate. The supernatant was removed to a volume of 25 μl.
2. The DNA-loaded ISPs were washed by filling the sample tube with 150 μL Annealing Buffer and gently mixed with the tip of a pipette.
3. The sample containing the DNA-loaded ISPs of step 2 were centrifuged for 2 minutes at a minimum of 15000 rcf. The supernatant was discarded, except for a final volume of 3 μL. The 3 μL volume was mixed by repeated pipetting.
4. 3 μL of Sequencing Primer (sold as a component of the Ion Sequencing Reagents Kit, (Life Technologies, Part No. 4468995) was added to the 3 μL volume of step 3. If the final volume of step 4 is less than 6 μL, the volume was adjusted by adding Annealing Buffer to a final volume of 6 μL. If adjustment is required, mix the sample well by pipetting.
5. The sample of step 4 was run on the following hybridization program on a thermocycler (for example a "QuickHyb Program") with the following temperature profile:
95° C. for 2 minutes; followed by 37° C. for 2 minutes.
6. 1 μL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes.
7. The loading protocol was then bifurcated based on the presence of companion particles in the loading protocol. If companion particles were to be used, the following steps were performed during incubation of the sample from step 6.
8. A solution (30 μL) containing companion particles (3.5 million) (here, SOLiD EZ Bead 6 um polystyrene beads) was transferred into a 200 μl PCR tube, to which 150 μL of 50% Annealing Buffer was added. The solution was vortexed and centrifuged for 2 minutes at a minimum of 15000 rcf. The supernatant was removed carefully so not to disturb the particle pellet.
9. Once the incubation period was complete, the incubated mixture of step 6 (~7 μL) was added to the tube containing companion particles (step 8).
10. The sample was sonicated for 10 seconds. Droplets may deposit on the interior wall of the tube. If this occurs, collect the liquid into one pool by a brief (1-2 seconds) spin in a centrifuge and then briefly mix using the tip of a pipette.
11. With the Chip on a flat surface, 7 μL of the sample (from step 10) was applied to the loading port (large port) of the Chip, dialing down the pipette to gently and slowly deposit the sample into the Chip. A good speed is about 1 μL every second. Residual liquid was removed from the outlet.
12. The Chip was then centrifuged at room temperature for 1 minute.
13. 4 μl of the loaded sample volume was removed and re-loaded (re-applied) to the chip port for a minimum of five cycles, while leaving some liquid in the chip to minimize air bubbles.
14. Steps 12 and 13 were repeated once.
15. All residual fluid was removed from the Chip.
16. The Chip was then washed 4 times with 50 μL of 50% Annealing Buffer to remove companion particles and unbound ISPs before inserting Chip into PGM™ Sequencer.
17. A PGM™ run was performed essentially according to the protocols provided in the Ion Sequencing Kit User Guide v2.0 (Life Technologies, Part No. 4468997), incorporated herein by reference in their entirety.

Example 9

The following discloses a non-limiting example of a method to prepare an Ion Torrent 316™ Chip (Life Technologies, Part No. 4462923) and method for enhancing nucleic acid loading on the Ion Torrent 316™ Chip for sequencing using an Ion Torrent PGM™ Sequencer (Life Technologies, Part No. 4462917).

Chip Preparation

1. A new Ion Torrent 316™ Chip was obtained and labeled appropriately to identify the experiment.
2. A chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).
3. The Chip was removed from the PGM™ sequencer and washed with 100 μL 100% Isopropanol (2-propanol) and then washed with 3× of 100 μL Annealing Buffer (sold as a component of the Ion PGM™ Reagents Kit, (Life Technologies, Part No. 4468994). Here, each washing step entailed a 2 minute spin on a microcentrifuge at 14,000 rpm (16873 rcf).

The proceeding steps required the preparation of nucleic-acid loaded beads (here, Ion Sphere Particles (ISPs) loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 20 million DNA-loaded ISPs or a full plate of ISPs prepared using the Ion Xpress™ Template Kit were transferred into a 200 μL PCR tube and 3 μL Ion Sphere™ Test Fragments from the Ion Control Material Kit (Life Technologies, Part No. 4466465) were added. If the DNA-loaded ISPs are in excess of 50 μL, Annealing Buffer (sold as a component of the Ion PGM™ Reagents Kit, (Life Technologies, Part No. 4468994) was added up to ~150 μL and centrifuged once to concentrate. The supernatant was removed to a volume of 25 μl.

2. The DNA-loaded ISPs were washed by filling the sample tube with 150 μL Annealing Buffer and gently mixed with the tip of a pipette.

3. The sample containing the DNA-loaded ISPs of step 2 were centrifuged for 2 minutes at a minimum of 15000 rcf. The supernatant was discarded, except for a final volume of 15 μL. The 15 μL volume was mixed by repeated pipetting.

4. 12 μL of Sequencing Primer (sold as a component of the Ion Sequencing Reagents Kit, (Life Technologies, Part No. 4468995) was added to the 15 μL volume of step 3. If the final volume of step 4 is less than 27 μL, the volume was adjusted by adding Annealing Buffer to a final volume of 27 μL. If adjustment is required, mix the sample well by pipetting.

5. The sample of step 4 was run on the following hybridization program on a thermocycler (for example a "QuickHyb Program") with the following temperature profile:
95° C. for 2 minutes; followed by 37° C. for 2 minutes.

6. 3 μL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes. The final volume should be about 30 μL.

7. The loading protocol was then bifurcated based on the presence of companion particles in the loading protocol. If companion particles were to be used, the following steps were performed during incubation of the sample from step 6.

8. A solution (70 μL) containing companion particles (5 million) (here, SOLiD EZ Bead 6 um polystyrene beads) was transferred into a 1.5 ml PCR tube, to which 500 μL of 50% Annealing Buffer was added. The solution was vortexed and centrifuged for 2 minutes at a minimum of 15000 rcf. The supernatant was removed carefully so not to disturb the particle pellet.

9. Once the incubation period was complete, the incubated mixture of step 6 (~30 μL) was added to the tube containing companion particles (step 8).

10. The sample was sonicated for 10 seconds. Droplets may deposit on the interior wall of the tube. If this occurs, collect the liquid into one pool by a brief (1-2 seconds) spin in a centrifuge and then briefly mix using the tip of a pipette.

11. With the Chip on a flat surface, 30 μL of the sample (from step 10) was applied to the loading port (large port) of the Chip, dialing down the pipette to gently and slowly deposit the sample into the Chip. A good speed is about 1 μL every second. Residual liquid was removed from the outlet.

12. The Chip was then centrifuged at room temperature for 1 minute.

13. 25 μl of the loaded sample volume was removed and re-loaded (re-applied) to the chip port for a minimum of five cycles, while leaving some liquid in the chip to minimize air bubbles.

14. Steps 12 and 13 were repeated once.

15. All residual fluid was removed from the Chip. In this instance, the chip was held at a 45-degree angle, to gently remove as much residual liquid as possible from the port of the chip. If residual liquid remains, the following steps were performed:
a) Hold the chip with the ports facing outward from your palm with the loading port being lower. b) Pipette as much liquid as possible from the loading port.
c) With a flick of the wrist, draw the remaining liquid to the loading port and remove
d) Repeat steps a)-c) until as much liquid is removed as possible.

16. The Chip was then washed 4 times with 50 μL of 50% Annealing Buffer to remove companion particles and unbound ISPs before inserting Chip into PGM™ Sequencer.

17. A PGM™ run was performed essentially according to the protocols provided in the Ion Sequencing Kit User Guide v2.0 (Life Technologies, Part No. 4468997), incorporated herein by reference in their entirety.

Example 10

The following discloses a non-limiting example of a method to prepare an Ion Torrent 318™ Chip (Life Technologies) and method for enhancing nucleic acid loading on the Ion Torrent 318™ Chip for sequencing using an Ion Torrent PGM™ Sequencer (Life Technologies, Part No. 4462917).

Chip Preparation

1. A new Ion Torrent 318™ Chip was obtained and labeled appropriately to identify the experiment.

2. A chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).

3. The Chip was removed from the PGM™ sequencer and washed with 100 μL 100% Isopropanol (2-propanol) and then washed with 3× of 100 μL Annealing Buffer (sold as a component of the Ion PGM™ Reagents Kit, (Life Technologies, Part No. 4468994). Here, each washing step entailed a 2 minute spin on a microcentrifuge at 14,000 rpm (16873 rcf).

The proceeding steps required the preparation of nucleic-acid loaded beads (here, Ion Sphere Particles (ISPs) loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 30 million DNA-loaded ISPs or a full plate of ISPs prepared using the Ion Xpress™ Template Kit were transferred into a 200 μL PCR tube and 5 μL Ion Sphere™ Test Fragments from the Ion Control Material Kit (Life Technologies, Part No. 4466465) were added. If the DNA-loaded ISPs are in excess of 50 μL, Annealing Buffer (sold as a component of the Ion PGM™ Reagents Kit, (Life Technologies, Part No. 4468994) was added up to ~150 μL and centrifuged once to concentrate. The supernatant was removed to a volume of 25 μl.

2. The DNA-loaded ISPs were washed by filling the sample tube with 150 μL Annealing Buffer and gently mixed with the tip of a pipette.

3. The sample containing the DNA-loaded ISPs of step 2 were centrifuged for 2 minutes at a minimum of 15000 rcf. The supernatant was discarded, except for a final volume of 15 μL. The 15 μL volume was mixed by repeated pipetting.

4. 12 μL of Sequencing Primer (sold as a component of the Ion Sequencing Reagents Kit, (Life Technologies, Part No. 4468995) was added to the 15 μL volume of step 3. If the final volume of step 4 is less than 27 μL, the volume was adjusted by adding Annealing Buffer to a final volume of 27 μL. If adjustment is required, mix the sample well by pipetting.

5. The sample of step 4 was run on the following hybridization program on a thermocycler (for example a "QuickHyb Program") with the following temperature profile:

95° C. for 2 minutes; followed by 37° C. for 2 minutes.

6. 3 μL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes. The final volume should be about 30 μL.

7. The loading protocol was then bifurcated based on the presence of companion particles in the loading protocol. If companion particles were to be used, the following steps were performed during incubation of the sample from step 6.

8. A solution (100 μL) containing companion particles (7.5 million) (here, SOLiD EZ Bead 6 um polystyrene beads) was transferred into a 1.5 ml PCR tube, to which 500 μL of 50% Annealing Buffer was added. The solution was vortexed and centrifuged for 2 minutes at a minimum of 15000 rcf. The supernatant was removed carefully so not to disturb the particle pellet.

9. Once the incubation period was complete, the incubated mixture of step 6 (~30 μL) was added to the tube containing companion particles (step 8).

10. The sample was sonicated for 10 seconds. Droplets may deposit on the interior wall of the tube. If this occurs, collect the liquid into one pool by a brief (1-2 seconds) spin in a centrifuge and then briefly mix using the tip of a pipette.

11. With the Chip on a flat surface, 30 μL of the sample (from step 10) was applied to the loading port (large port) of the Chip, dialing down the pipette to gently and slowly deposit the sample into the Chip. A good speed is about 1 μL every second. Residual liquid was removed from the outlet.

12. The Chip was then centrifuged at room temperature for 1 minute.

13. 25 μl of the loaded sample volume was removed and slowly re-loaded (re-applied) to the chip port for a minimum of five cycles, while leaving some liquid in the chip to minimize air bubbles.

14. Steps 12 and 13 were repeated once.

15. All residual fluid was removed from the Chip. In this instance, the chip was held at a 45-degree angle, to gently remove as much residual liquid as possible from the port of the chip. If residual liquid remains, the following steps were performed:

a) Hold the chip with the ports facing outward from your palm with the loading port being lower. b) Pipette as much liquid as possible from the loading port.

c) With a flick of the wrist, draw the remaining liquid to the loading port and remove d) Repeat steps a)-c) until as much liquid is removed as possible.

16. The Chip was then washed 4 times with 50 μL of 50% Annealing Buffer to remove companion particles and unbound ISPs before inserting Chip into PGM™ Sequencer.

17. A PGM™ run was performed essentially according to the protocols provided in the Ion Sequencing Kit User Guide v2.0 (Life Technologies, Part No. 4468997), incorporated herein by reference in their entirety.

Example 11

The following discloses a non-limiting example of a method to prepare an Ion Torrent 316™ Chip (Life Technologies, Part No. 4462923) and method for enhancing nucleic acid loading on the Ion Torrent 316™ Chip for sequencing using an Ion Torrent PGM™ Sequencer (Life Technologies, Part No. 4462917).

Chip Preparation

1. A new Ion Torrent 316™ Chip was obtained and labeled appropriately to identify the experiment.

2. A chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).

3. The Chip was removed from the PGM™ sequencer and washed with 100 μL 100% Isopropanol (2-propanol) and then washed with 3× of 100 μL Annealing Buffer (sold as a component of the Ion PGM™ Reagents Kit, (Life Technologies, Part No. 4468994). Here, each washing step entailed a 2 minute spin on a microcentrifuge at 14,000 rpm (16873 rcf).

The proceeding steps required the preparation of nucleic-acid loaded beads (here, Ion Sphere Particles (ISPs) loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 20 million DNA-loaded ISPs or a full plate of ISPs prepared using the Ion Xpress™ Template Kit were transferred into a 200 μl, PCR tube and 3 μl, Ion Sphere™ Test Fragments from the Ion Control Material Kit (Life Technologies, Part No. 4466465) were added. If the DNA-loaded ISPs are in excess of 50 μL, Annealing Buffer (sold as a component of the Ion PGM™ Reagents Kit, (Life Technologies, Part No. 4468994) was added up to ~150 μL and centrifuged once to concentrate. The supernatant was removed to a volume of 25 μl.

2. The DNA-loaded ISPs were washed by filling the sample tube with 150 μL Annealing Buffer and gently mixed with the tip of a pipette.

3. The sample containing the DNA-loaded ISPs of step 2 were centrifuged for 2 minutes at a minimum of 15000 rcf. The supernatant was discarded, except for a final volume of 15 μL. The 15 μL volume was mixed by repeated pipetting.

4. 12 μL of Sequencing Primer (sold as a component of the Ion Sequencing Reagents Kit, (Life Technologies, Part No. 4468995) was added to the 15 μL volume of step 3. If the final volume of step 4 is less than 27 μL, the volume was adjusted by adding Annealing Buffer to a final volume of 27 μL. If adjustment is required, mix the sample well by pipetting.

5. The sample of step 4 was run on the following hybridization program on a thermocycler (for example a "QuickHyb Program") with the following temperature profile: 95° C. for 2 minutes; followed by 37° C. for 2 minutes.

6. 3 µL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes. The final volume should be about 30 µL.

7. The sample was sonicated for 10 seconds. Droplets may deposit on the interior wall of the tube. If this occurs, collect the liquid into one pool by a brief (1-2 seconds) spin in a centrifuge and then briefly mix using the tip of a pipette.

8. With the Chip on a flat surface, 30 µL of the sample (from step 6) was applied to the loading port (large port) of the Chip, dialing down the pipette to gently and slowly deposit the sample into the Chip. A good speed is about 1 µL every second. Residual liquid was removed from the outlet.

9. The Chip was then centrifuged at room temperature for 1 minute.

10. 20 µl of the loaded sample volume was removed and slowly re-loaded (re-applied) to the chip port for a minimum of five cycles, while leaving some liquid in the chip to minimize air bubbles.

11. The Chip was then centrifuged at room temperature for 1 minute.

12. Steps 10 and 11 were repeated once.

13. All residual fluid was removed from the Chip. In this instance, the chip was held at a 45-degree angle, to gently remove as much residual liquid as possible from the port of the chip. If residual liquid remains, the following steps were performed:
a) Hold the chip with the ports facing outward from your palm with the loading port being lower. b) Pipette as much liquid as possible from the loading port.
c) With a flick of the wrist, draw the remaining liquid to the loading port and remove
d) Repeat steps a)-c) until as much liquid is removed as possible.

14. The Chip was then washed 1 time with 50 µL of 50% Annealing Buffer before inserting Chip into PGM™ Sequencer.

15. A PGM™ run was performed essentially according to the protocols provided in the Ion Sequencing Kit User Guide v2.0 (Life Technologies, Part No. 4468997), incorporated herein by reference in their entirety.

Example 12

The following discloses a non-limiting example of a method to prepare an Ion Torrent 316™ Chip (Life Technologies, Part No. 4462923) and method for enhancing nucleic acid loading on the Ion Torrent 316™ Chip for sequencing using an Ion Torrent PGM™ Sequencer (Life Technologies, Part No. 4462917).

Chip Preparation

1. A new Ion Torrent 316™ Chip was obtained and labeled appropriately to identify the experiment.

2. A chip check and calibration on the PGM™ sequencer was performed essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994).

3. The Chip was removed from the PGM™ sequencer and washed with 100 µL 100% Isopropanol (2-propanol) and then washed with 3× of 100 µL Annealing Buffer (sold as a component of the Ion PGM™ Reagents Kit, (Life Technologies, Part No. 4468994). Here, each washing step entailed a 2 minute spin on a microcentrifuge at 14,000 rpm (16873 rcf).

The proceeding steps required the preparation of nucleic-acid loaded beads (here, Ion Sphere Particles (ISPs) loaded with DNA). Procedures to perform and generate DNA-loaded ISPs can be practiced essentially according to the protocols provided in the Ion Xpress™ Template Kit User Guide v2.0 (Life Technologies, Part No. 4469004), hereby incorporated by reference in its entirety, using the Ion Xpress™ Template Kit (Life Technologies, Part No. 4469001), hereby incorporated by reference in its entirety.

Enhanced Nucleic Acid Loading (ISPs)

1. 20 million DNA-loaded ISPs or a full plate of ISPs prepared using the Ion Xpress™ Template Kit were transferred into a 200 µL PCR tube and 3 µL Ion Sphere™ Test Fragments from the Ion Control Material Kit (Life Technologies, Part No. 4466465) were added. If the DNA-loaded ISPs are in excess of 50 µL, Annealing Buffer (sold as a component of the Ion PGM™ Reagents Kit, (Life Technologies, Part No. 4468994) was added up to ~150 µL and centrifuged once to concentrate. The supernatant was removed to a volume of 25 µl.

2. The DNA-loaded ISPs were washed by filling the sample tube with 150 µL Annealing Buffer and gently mixed with the tip of a pipette.

3. The sample containing the DNA-loaded ISPs of step 2 were centrifuged for 2 minutes at a minimum of 15000 rcf. The supernatant was discarded, except for a final volume of 15 µL. The 15 µL volume was mixed by repeated pipetting.

4. 12 µL of Sequencing Primer (sold as a component of the Ion Sequencing Reagents Kit, (Life Technologies, Part No. 4468995) was added to the 15 µL volume of step 3. If the final volume of step 4 is less than 27 µL, the volume was adjusted by adding Annealing Buffer to a final volume of 27 µL. If adjustment is required, mix the sample well by pipetting.

5. The sample of step 4 was run on the following hybridization program on a thermocycler (for example a "QuickHyb Program") with the following temperature profile: 95° C. for 2 minutes; followed by 37° C. for 2 minutes.

6. 3 µL of Sequencing Polymerase (sold as a component of the Ion Sequencing Reagents Kit, (Life Technologies, Part No. 4468995) was added to the sample after performing the QuickHyb Program and the sample was mixed and incubated at room temperature for 5 minutes. The final volume should be about 30 µL.

7. The sample was sonicated for 10 seconds. Droplets may deposit on the interior wall of the tube. If this occurs, collect the liquid into one pool by a brief (1-2 seconds) spin in a centrifuge and then briefly mix using the tip of a pipette.

8. With the Chip on a flat surface, 30 µL of the sample (from step 6) was applied to the loading port (large port) of the Chip, dialing down the pipette to gently and slowly deposit the sample into the Chip. A good speed is about 1 µL every second. Residual liquid was removed from the outlet.

9. The Chip was then centrifuged at room temperature for 1 minute.

10. 25 µl of the loaded sample volume was removed and slowly re-loaded (re-applied) to the chip port for a minimum of five cycles, while leaving some liquid in the chip to minimize air bubbles.

11. The Chip was then centrifuged at room temperature for 1 minute.

12. Steps 10 and 11 were repeated once.

12. After the final centrifugation, check to ensure no large bubbles are trapped on the chip. If present, the chip was flushed with 100 μl of 50% Annealing Buffer before inserting Chip into PGM™ Sequencer.

13. A PGM™ run was performed essentially according to the protocols provided in the Ion Sequencing Kit User Guide v2.0 (Life Technologies, Part No. 4468997), incorporated herein by reference in their entirety.

Example 13

Table 1 presents data obtained from nucleic acid sequencing experiments and reports the quality of the nucleic acid sequence data using the methods disclosed herein. Quality metrics such as peak signal, 100Q17 and AQ17 are presented. Various companion particles were used in the sequencing experiments and are reported under bead description. The bead size as reported in the Table refers to companion particles with a range of 4.8 um to 7.1 um average cross-sectional diameter. The data was generated using Ion Torrent 316™ Chips (Life Technologies, Part No. 4462923).

TABLE 1

| Run name | Bead description | Bead size | 100Q17 | AQ17 | Peak signal |
| --- | --- | --- | --- | --- | --- |
| LEA 191 | SOLiD EZ bead enricher (dynal) | 6 | 2,845,898 | 620,601,222 | 65 |
| HoF 631 | SOLiD EZ bead enricher (dynal) | 6 | 2,853,418 | 626,984,623 | 69 |
| GAR 659 | Surfactant free blue sulphate (IDC/mol probes) | 4.8 | 2,542,949 | 554,461,510 | 65 |
| LEN 661 | Surfactant free blue sulphate (IDC/mol probes) | 4.8 | 2,872,290 | 631,110,279 | 65 |
| KUB 425 | Surfactant free blue sulphate (IDC/mol probes) | 6.3 | 2,148,266 | 465,699,949 | 62 |
| HOF 626 | Surfactant free blue sulphate (IDC/mol probes) | 6.3 | 2,186,206 | 465,615,985 | 59 |
| LEA 188 | Surfactant free yell green sulphate (IDC/mol probes) | 5.2 | 2,340,898 | 507,212,844 | 70 |
| HOF 628 | Surfactant free yell green sulphate (IDC/mol probes) | 5.2 | 2,321,351 | 502,490,341 | 69 |
| GAR 660 | SPHERO polystyrene blue (Spherotech) | 7.1 | 2,801,621 | 621,971,702 | 68 |
| LEN 662 | SPHERO polystyrene blue (Spherotech) | 7.1 | 2,869,779 | 630,650,758 | 68 |
| LEA 192 | SPHERO polystyrene particles (Spherotech) | 6.8 | 2,879,481 | 632,231,475 | 69 |
| HOF 632 | SPHERO polystyrene particles (Spherotech) | 6.8 | 3,025,096 | 669,652,719 | 69 |
| GAR 661 | white nonionic polystyrene latex (IDC/mol probes) | 5.2 | 2,739,361 | 610,272,589 | 69 |
| LEN 663 | white nonionic polystyrene latex (IDC/mol probes) | 5.2 | 2,456,685 | 541,576,722 | 65 |

Example 14

A sequencing chip can be loaded with a sample following enrichment of the sample. The sample may or may not include companion particles. Before starting, the following stock solutions are prepared:

50% Annealing buffer: in a 15-mL conical tube, combine 5 mL of Annealing buffer with 5 mL of nuclease-free water.

Defoaming solution: in a 15-mL conical tube, combine 5 mL of 100% isopropanol with 2.5 mL of Annealing buffer and 2.5 mL of nuclease-free water.

Prepare the Chip for Loading
1. Place the Ion Proton I™ Chip (available from ION Torrent) on a stable surface such as a benchtop.
2. In a 1.5 mL tube, combine 64 μL of 50% Annealing buffer with 6 μL of foaming solution.
3. Create mock foam by injecting air into the 70 μL sample using a Rainin® SR-L200F pipette set to dispense 70 μL. Next, break the large bubbles into smaller bubbles by rapidly pipetting for ~10 seconds. Repeat this step 2 more times.

The sample should consist of foam. The foam is ready when it can be aspirated into the pipette tip as a white, stable mixture of very small bubbles without aqueous solution collecting at the tip of the pipette.

Be careful not to over-inject air; the final volume of foam should be approximately 300 μL.

4. Inject 70 μL of mock foam into the chip flow cell. Discard the liquid that comes out of the opposite port.
5. Proceed immediately to loading the chip.

Load the Sample on the Chip
1. Add 6 μL of Foaming solution to the 64 μL enriched Ion Proton™ I ISP sample and mix, transfer to a 1.5 mL tube.
2. Foam up the ISP sample by injecting air into the 70 μL sample using a Rainin® SR-L200F pipette set to dispense 70 μL. Next, break the large bubbles into smaller bubbles by rapidly pipetting for ~10 seconds. Repeat this step 2 more times.

The sample should now consist of foam. The foam is ready when it can be aspirated into the pipette tip as a white, stable mixture of very small bubbles without aqueous solution collecting at the tip of the pipette.

Be careful not to over-inject air; the final volume of foam should be approximately 300 μL.

It is convenient to use the same pipette tip throughout this part of the loading procedure.
3. Aspirate 75 μL of foam into the pipette tip. Using a quick pipetting motion, inject the foam into the flow cell. Discard the mock foam that comes out of the opposite port.
4. Insert the chip into the chip-holding adapter and vortex at 3000 rpm for 2 minutes.

If using an IKA MS3 vortexer, the machine should be in 'mode B' to achieve 3000 rpm. To go into 'mode B', hold down the Start button while pressing the Power button when turning on the vortexer. Vortex Genie vortexers should be run at the maximum setting.

5. Set the pipette to 65 μL. Pipette the foamy ISP solution up and down rapidly to make sure the foam is the right consistency. It is desirable to 're-foam' in this manner before every foam injection.
6. Inject 65 μL of foam into the flow cell. Save the used foam that comes out of the opposite port by pipetting it into a 1.5 mL tube labeled 'used foam'.
7. Vortex the chip for 2 minutes.
8. Repeat steps 5-7 one or two more times until all or most of the foam has been used.

9. After the last foam injection, if there is a small amount of foam left in the 1.5 mL tube, transfer it to the 'used foam' tube.
10. Pipette the 'used foam' up and down rapidly for ~10 seconds to ensure that the foam is the right consistency.
11. Inject 65 µL of foam from the 'used foam' tube into the flow cell. Add the foam that comes out of the opposite port to the 'used foam' tube.
12. Vortex the chip for 2 minutes.
13. Repeat steps 11-12 two or three more times until all or most of the foam has been used. For these injections, discard the foam that comes out of the opposite port.

Flush Out the Foam and Load Polymerase
1. Flush the chip with 100 µL, of a Defoaming solution. Discard the solution that comes out of the opposite port.
2. Some bubbles will remain along the edges of the flow cell. Remove these by slowly withdrawing ~75% of the defoaming solution from the flow cell, then slowly pipetting it back in.

It is easiest to perform this step by dialing the pipette and holding the chip at an angle (rather than flat on the bench) such that the force of gravity pulls the solution towards the pipetting port.

Pay attention to the bubbles along the edge of the flow cell. The defoaming solution should disrupt these bubbles as it is withdrawn from the flow cell.

When pipetting the defoaming solution back in, the fluid meniscus should 'hug' the edge of the flow cell without allowing air pockets to form.

The defoaming solution may not completely fill the flow cell once it has been dialed back in. The flushing procedure in the next step will usually remove any air pockets that remain.
3. Flush the chip 4 times with 100 µL, of 50% Annealing buffer. Be careful not to introduce air bubbles. After each flushing step, remove the liquid that comes out of the opposite port.
4. Combine 6 µL of Ion Proton™ I Sequencing 200 Polymerase with 65 µL, of 50% Annealing buffer.
5. Slowly inject this solution into the flow cell (this step can be performed by dialing the pipette).
6. After 5 minutes, clamp the chip into the Ion Proton™ Sequencer and proceed with starting the run.

Example 15

A sequencing chip can be loaded with a sample following enrichment of the sample. The sample may or may not include companion particles. Following formation of the enriched sample, a chip can be loaded using centrifugation.
1. With the chip on a flat surface, dial in 30 µL of sample into the loading port (large port) of the chip, making sure that no air bubbles are introduced. Remove residual liquid from outlet.
2. Centrifuge the chip for 30 seconds with the tab facing in.
3. Mix the sample in the chip: Tilt the chip 45 degrees so that the loading port is the lower port. Set the pipette to ~30 µl and pipette the liquid in and out 3 times. Choose a pipetting rate so that most of liquid is being moved but no air bubbles are introduced into the chip.
4. Centrifuge for 30 seconds, with the tab facing out.
5. Repeat step 3, followed by a final 30 second spin with the tab in.
6. Remove the liquid from the chip: Holding the chip at a 45-degree angle, gently remove as much liquid as possible from the port by dialing the liquid out. If all the liquid does not come out, put the chip in the centrifuge with the tab facing out, and perform a quick ~5 sec spin. If the liquid is not quite in the port area, firmly tap the chip against the table a few times with the point of impact being the tab. This should bring the liquid to the loading port area for pipette removal. Do not flush the chip.
7. Start the PGM run.

Example 16

A sequencing chip can be loaded with a sample following enrichment of the sample. The sample may or may not include companion particles.
1. After washing 30M enriched beads in PBST, decant the sample until approximately 15 uL are remaining. To this, add 12 uL of Sequencing Primer and place tube in thermal cycler. Run 'FastHyb' program.
2. After chip check and calibration, flush the chip with 200 uL of 100% isopropyl alcohol (surfynol) followed by 200 uL of 50% PBST. Repeat the 50% PBST flushes for a total of 3 flushes.
3. Take sample tube off of thermal cycler and add 3 uL of sequencing polymerase. Mix well and allow the sample to incubate for 5 minutes at room temperature.
4. After incubation, add 30 uL of 50% PBST to the sample for a final volume of 60 uL.
5. Remove liquid from the flowcell.
6. Dial 30 uL of the diluted sample into the chip.
7. Spin for 1 minute in a (Galaxy) centrifuge.
8. Remove chip from centrifuge and add (dial in) the remaining 30 uL of sample. Collect the 'flow-through' (the best way to do this is to dial up the liquid) that exits the chip and inject this into the chip again. Collect the flow-through once more and set it aside.
9. Spin for one minute.
10. Repeat steps 7-8 four more times (for a total of five 'flow-through' steps (2×30 uL each)).
11. After the final spin, the chip is ready to be loaded on the PGM. No flushing or backfilling is utilized.
Notes:
1. Injections into the chip should be dialed in. This should not take longer than 10 seconds per 30 uL.
2. Collect the waste from the reservoir through dialing up (to avoid bubbles).
3. The volume of the waste decreases slowly over time as it is difficult to collect every last microliter after each flow. Do not top this up with 50% PBST, simply continue to flow through whatever volume is collected.

Example 17

A sequencing chip can be loaded with a sample following enrichment of the sample. The sample may or may not include companion particles.
1. Obtain a new 318 chip, label appropriately to identify the experiment.
2. Perform chip check and calibration on the PGM.
3. Remove the chip and wash with 100 µL 100% Isopropanol (2-propanol) and then wash the chip 3× with 100 µL Annealing Buffer.

Note: When your chip is not in the PGM and clamped down, add a dummy chip to prevent air pockets from forming due to back flow in the squid lines.

Post-Enrichment: Isolate 20 Million SNAPPs (318)
1. Transfer SNAPPS into a 200 µL PCR tube and add 5 µL TFs. If SNAPPs are in more than 50 µL, add Annealing Buffer up to ~150 µL and spin once to concentrate, then remove supernatant down to 25 µl.
2. Wash SNAPPS by filling the tube with 150 µL Annealing Buffer and tip mix.

3. Centrifuge 2 minutes @ a minimum of 15000 rcf and leave 15 µL in the tube. Mix well by pipetting.
4. Add 12 µL Sequencing Primer. Confirm volume is 27 µL; if less, add Annealing Buffer until the final volume is 27 µL. Mix well by pipetting.
5. Run the QuickHyb Program on the cycler (95° C., 2 min; 37° C., 2 min)
6. Add 3 µL of Sequencing Polymerase, tip mixing well. Incubate at room temp for 5 minutes. The final volume should be about 30 ul.
7. Centrifuge chip upside-down, with tab facing out for 30 seconds to empty buffer from chip (using UP adapter placed over chip). Wipe off excess buffer on UP adapter with Kimwipe.
8. Place the chip on a flat surface, dial in 30 µL of sample into the loading port (large port) of the chip.
9. Centrifuge your chip for 1 minute with the tab facing in.
10. Place the adapter onto the chip and centrifuge the chip upside-down with tab facing out for 1 min.
11. Remove the chip from the adapter and pipette the liquid from the adapter well and reload into the chip. (Note: Add in 50% annealing buffer to fill in any open space in the chip)
12. Centrifuge the chip right side up for 1 min with the tab facing in.
13. Repeat step 10
14. Place the empty chip on the PGM and start the run.

Example 18

A sequencing chip can be loaded with a sample following enrichment of the sample. The sample may or may not include companion particles.
Post-Enrichment
1. Transfer SNAPPS into a 200 µL PCR tube and add 5 µL TFs. If SNAPPs are in more than 50 µL, add Annealing Buffer up to ~200 µL and spin once to concentrate, and then remove supernatant down to 254
2. Wash SNAPPS by filling the tube with (150-200 µL) Annealing Buffer and tip mix.
3. Centrifuge 2 minutes @ a minimum of 15000 rcf and leave 15 µL in the tube. Mix well by pipetting.
4. Add 12 µL Sequencing Primer. Confirm volume is 27 µL; if less, add Annealing Buffer until the final volume is 27 µL. Mix well by pipetting.
5. Run the QuickHyb Program on the cycler (95° C., 2 min; 37° C., 2 min)
6. Add 3 µL of Sequencing Polymerase, tip mixing well. Incubate at room temp for 5 minutes. The final volume should be about 30 ul. A slightly higher volume (up to 35 uL) is better than a lower volume. If lower, adjust the volume with annealing buffer as is useful.
7. With the chip on a flat surface, dial in 30 µL of sample into the loading port (large port) of the chip, making sure that no air bubbles are entrapped. Remove residual liquid from outlet.
8. Centrifuge your chip for 1 minute with the tab facing in.
9. Leaving the chip in the bucket, add the weighted adapter to the top of the chip. Add 100 ul of 50% annealing buffer to the port area opposite the weighted side.
10. Place the chip into the centrifuge. Make sure the weighted side is facing the outer edge of the centrifuge before spinning. Centrifuge for 30 seconds.
11. Lift the adapter off the chip surface, rotate 180 degrees, and place back down on top of the chip. Once again, make sure the weighted side is facing the outer edge of the centrifuge before spinning. This amounts to the chip rotating before each spin, but the adapter staying in the same orientation. Centrifuge for 30 seconds.
12. Repeat step 11 three more times.
13. Remove the adapter from the top of the chip and remove the excess liquid from the port area.
14. Perform a final 1 minute spin with the tab facing in.
15. Start the PGM run.

In a first aspect, a method for analyzing a biomolecule includes forming a foam from a sample including a plurality of biomolecule-enhanced particles, applying at least a portion of the foam to an array, and vortexing the array.

In an example of the first aspect, forming the foam includes injecting air into the sample. For example, forming the foam can include aspirating the foam into a pipette tip repeatedly.

In another example of the first aspect and the above examples, the method further includes applying another portion of the foam to the array. In an example, the method further includes vortexing the array after applying the another portion of the foam. In an additional example, the method further includes repeating applying another portion of the foam and vortexing.

In a further example of the first aspect and the above examples, the method further includes removing used foam following vortexing. In an example, the method further includes placing the array in a device. The method can further include analyzing the biomolecules on the biomolecule-enhanced particles.

In a second aspect, a method of analyzing a biomolecule includes applying at least a portion of a sample to an array and centrifuging the array and repeating applying and centrifuging.

In an example of the second aspect, applying includes pipetting the at least a portion of the sample into a flow cell formed over the array.

In another example of the second aspect and the above examples, repeating includes withdrawing and reapplying the at least a portion of the sample to the array.

In a further example of the second aspect and the above examples, repeating includes applying another portion of the sample to the array.

In an additional example of the second aspect and the above examples, applying includes pipetting an amount of the sample that is not greater than the volume of a flow cell formed over the array.

In an example of the second aspect and the above examples, applying includes pipetting an amount of the sample that is greater than the volume of a flow cell formed over the array and collecting a pass-through portion of the sample.

In another example of the second aspect and the above examples, centrifuging includes centrifuging with the array facing a center point of the centrifuge.

In a further example of the second aspect and the above examples, centrifuging includes centrifuging with the array facing away from a center point of the centrifuge.

In an additional example of the second aspect and the above examples, centrifuging includes centrifuging with the array perpendicular to a plane of rotation.

In an example of the second aspect and the above examples, centrifuging includes centrifuging with the array tilted relative to a plane of rotation.

In another example of the second aspect and the above examples, the array is tilted at an angle not greater than 90°. For example, the array can be tilted at an angle of at least 15°.

In a third aspect, a method for depositing a plurality of particles into a plurality of reaction chambers includes forming a particle mixture including a plurality of sample particles having a first average diameter and a plurality of companion particles having a second average diameter, contacting the particle mixture with a surface including a plurality of reaction chambers having entries, wherein the average cross sectional diameter of the entries of the plurality of reaction chambers is greater than the first average diameter but less than the second average diameter.

In an example of the third aspect, the contacting includes depositing a sample particle of the particle mixture into a percentage of the reaction chambers. For example, the percentage is increased relative to the percentage of reaction chambers that are filled by a control particle mixture that does not include companion particles.

In another example of the third aspect and the above examples, at least one of the reaction chambers contains no greater than one sample particle.

In a further example of the third aspect and the above examples, the contacting includes depositing no more than one sample particle in at least one reaction chamber.

In an additional example of the third aspect and the above examples, the contacting includes depositing each of at least two sample particles into different reaction chambers.

In an example of the third aspect and the above examples, the method further includes separating at least one companion particle from the surface, optionally without dislodging at least one sample particle from at least one reaction chamber.

In another example of the third aspect and the above examples, the method further includes agitating the particle mixture after contacting the surface.

In a further example of the third aspect and the above examples, the surface comprises an array. For example, the array can include a bead array, a slide, a microfluidic array, a nanofluidic array, a chip or a semiconductor based array.

In an additional example of the third aspect and the above examples, at least one of the reaction chambers comprises a channel, groove, pore, nanopore, well or microwell.

In a further example of the third aspect and the above examples, the particle mixture comprises about 80% to about 98% by weight sample particles.

In an additional example of the third aspect and the above examples, the companion particles comprise 15% or less of the total number of particles in the particle mixture.

In an example of the third aspect and the above examples, the surface comprises about 1 million to about 3 billion reaction chambers.

In another example of the third aspect and the above examples, the method further includes removing at least some portion of the particle mixture from the surface, optionally without dislodging at least one sample particle from the at least one reaction chamber of the surface.

In a further example of the third aspect and the above examples, at least one sample particle comprises a nucleic acid molecule attached to at least one bead. For example, the at least one bead can include silica, glass, coated glass, coated polyacrylamide, acrylamide, nylon, plastic, ceramic, polystyrene, porous silicon, or a combination thereof. In an example, the at least one bead includes a label, dye, magnet or detectable signal.

In an additional example of the third aspect and the above examples, at least one companion particle comprises silica, glass, coated glass, coated polyacrylamide, acrylamide, nylon, plastic, ceramic, polystyrene, porous silicon, or a combination thereof.

In an example of the third aspect and the above examples, at least one companion particle is inert.

In another example of the third aspect and the above examples, the method further includes applying a sequencing polymerase or a sequencing primer to the particle mixture.

In a further example of the third aspect and the above examples, the method further includes applying a foaming solution to the particle mixture.

In an additional example of the third aspect and the above examples, the method further includes performing one or more nucleic acid sequencing reactions on the at least one sample particle. In an example, the one or more one or more nucleic acid sequencing reactions can include single-stranded or bi-directional sequencing. In another example, the one or more nucleic acid sequencing reactions can identify at least one mutation in the sample particle.

In a fourth aspect, a sequencing component includes an array of wells and a plurality of biomolecule-enriched particles disposed in the wells in a 1:1 relationship, wherein the plurality of biomolecule-enriched particles are loaded into the wells using a method of any one of the above described aspects or associated examples.

In a fifth aspect, a method of analyzing a biomolecule includes applying a reagent to a sequencing component including an array in which a plurality of biomolecule-enriched particles is disposed, the plurality of biomolecule-enriched particles loaded into the array using a method of any one of the above aspects or associated examples and detecting a change in local environments proximate to one or more of the plurality of biomolecule-enriched particles.

Throughout this application various publications, patents, or patent applications are referenced. The disclosures of these publications, patents, or patent applications in their entireties are hereby incorporated by reference into this application in order to more fully describe the state of the art to which this invention pertains.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition or description is set forth herein that is contrary to or otherwise inconsistent with any definition set forth in the patents, patent applications, published applications, and other publications that are herein incorporated by reference, the definition or description set forth herein prevails over the definition that is incorporated by reference. It will be appreciated that there is an implied "about" prior to the temperatures, concentrations, times, etc., discussed in the present teachings, such that slight and insubstantial deviations are within the scope of the present teachings herein.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive- or and not to an exclusive- or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed:

1. A method for analyzing a biomolecule, the method comprising: forming a foam from a sample including a plurality of biomolecule-enhanced particles; applying at least a portion of the foam to an array; vortexing the array; and analyzing the biomolecules on the biomolecule-enhanced particles.

2. The method of claim 1, wherein forming the foam includes injecting air into the sample.

3. The method of claim 1, wherein forming the foam includes aspirating the foam into a pipette tip repeatedly.

4. The method of claim 1, further comprising applying another portion of the foam to the array.

5. The method of claim 4, further comprising vortexing the array after applying the another portion of the foam.

6. The method of claim 5, further comprising repeating applying another portion of the foam and vortexing.

7. The method of claim 1, further comprising removing used foam following vortexing.

8. The method of claim 7, further comprising placing the array in a device.

\* \* \* \* \*